United States Patent
Curtis et al.

(10) Patent No.: US 7,276,607 B2
(45) Date of Patent: Oct. 2, 2007

(54) 5-HT$_7$ RECEPTOR ANTAGONISTS

(75) Inventors: Neil Roy Curtis, Buntingford (GB); Peter Alan Hunt, Saffron Walden (GB); Janusz Jozef Kulagowski, Sawbridgeworth (GB)

(73) Assignee: Merck Sharp & Dohme Limited, Hoddesdon (GB)

( * ) Notice: Subject to any disclaimer, the term of this patent is extended or adjusted under 35 U.S.C. 154(b) by 478 days.

(21) Appl. No.: 10/497,617

(22) PCT Filed: Nov. 29, 2002

(86) PCT No.: PCT/GB02/05396

§ 371 (c)(1),
(2), (4) Date: Jun. 2, 2004

(87) PCT Pub. No.: WO03/048118

PCT Pub. Date: Jun. 12, 2003

(65) Prior Publication Data

US 2005/0080077 A1   Apr. 14, 2005

(30) Foreign Application Priority Data

Dec. 3, 2001   (GB) ................... 0128885.1

(51) Int. Cl.
*C07D 211/68* (2006.01)
*C07D 211/80* (2006.01)
*C07D 221/02* (2006.01)

(52) U.S. Cl. .................. 546/139; 546/212; 546/192

(58) Field of Classification Search ............... 546/139, 546/192, 194, 212
See application file for complete search history.

(56) References Cited

FOREIGN PATENT DOCUMENTS

WO   WO 97 29097 A   8/1997
WO   WO 97 48681 A   12/1997

OTHER PUBLICATIONS

R. Stragies, et al.: "Enantioselective synthesis of tetraponerines by Pd—and Ru-catalysed domino reactions" Journal of the Americna Chemical Society, vol. 122, No. 40, Sep. 26, 2000, pp. 9584-9591.

*Primary Examiner*—Rita Desai
(74) *Attorney, Agent, or Firm*—J. Eric Thies; William Krovatin

(57) ABSTRACT

Substituted carbocyclic sulphonamide derivatives of formula (I), in which n is 0 or 1 and the other variables are as defined in the claims, are selective 5-HT$_7$ receptor antagonists and are thereby effective in the treatment of a variety of neurological conditions, including depression and sleep disorders.

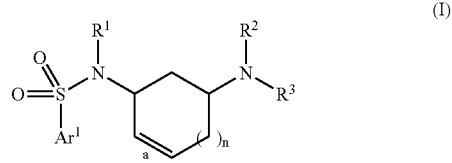

8 Claims, No Drawings

5-HT₇ RECEPTOR ANTAGONISTS

CROSS REFERENCE TO RELATED APPLICATIONS

This application is a U.S. National Phase application under 35 U.S.C. § 371 of PCT Application No. PCT/GBO2/05396, filed Nov. 29, 2002, which claims priority under 35 U.S.C. § 119 from GB Application No.0128885.1, filed Dec. 3, 2001.

The present invention relates to a class of sulphonamide derivatives which act on serotonin receptors (also known as 5-hydroxytryptamine or 5-HT receptors). More particularly, the invention concerns aryl- and heteroarylsulphonamide derivatives wherein the sulphonamide group is a substituent on a cycloalkane or cycloalkene ring which additionally bears an amino substituent. These compounds are selective antagonists of the human 5-HT₇ receptor and are therefore useful as pharmaceutical agents, especially in the treatment and/or prevention of adverse conditions of the central nervous system, such as depression, anxiety, sleep disorders and psychotic disorders such as schizophrenia.

The compounds according to the present invention are potent and selective 5-HT₇ receptor antagonists having a human 5-HT₇ receptor binding affinity ($K_i$) of 500 nM or less, typically of 100 nM or less and preferably of 50 nM or less. The compounds of the invention may possess at least a 10-fold selective affinity, suitably at least a 20-fold selective affinity and preferably at least a 50-fold selective affinity, for the human 5-HT₇ receptor relative to the other human 5-HT receptors (in particular the $5\text{-}HT_{1A}$, $5\text{-}HT_{1B}$ and $5\text{-}HT_{2A}$ receptors) and to the human dopamine $D_2$ receptor. By virtue of this selectivity, it is possible to provide treatments for the above-mentioned disorders having fewer or different side effects in comparison to known treatments for these disorders.

WO97/29097, WO97/48681 and WO97/49695 disclose various sulphonamide derivatives to be 5-HT₇ receptor antagonists, but do not disclose or suggest compounds in accordance with the present invention.

In accordance with the invention, there is provided a compound of formula I:

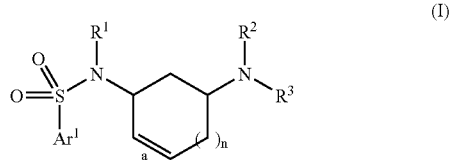

(I)

wherein:

n is 0 or 1;

bond a may be single or double, but is single when n is 1;

$Ar^1$ represents phenyl, naphthyl or heteroaryl, any of which optionally bears up to 3 substituents independently selected from halogen, CN, $NO_2$, $CF_3$, $R^4$, $OR^5$, $N(R^5)_2$, $CO_2R^5$, $COR^5$ and $CON(R^5)_2$;

$R^1$ represents $C_{1-6}$alkyl, $C_{2-6}$alkenyl, $C_{3-6}$cycloalkyl or $C_{3-6}$cycloalkyl$C_{1-2}$alkyl;

$R^2$ and $R^3$ independently represent H, $C_{1-6}$alkyl, $C_{3-6}$cycloalkyl or $C_{3-6}$cycloalkyl$C_{1-6}$alkyl, any of which is optionally substituted with halogen, CN, $NO_2$, $CF_3$, Ar, OAr, $OR^5$, $N(R^5)_2$, $CO_2R^5$, $COR^5$ or $CON(R^5)_2$; or $R^2$ and $R^3$ complete a mono- or bicyclic heterocyclic ring system of 5-10 members, up to 2 of which are selected from N, O and S, including the nitrogen atom to which $R^2$ and $R^3$ are attached, said ring system optionally bearing up to 3 substituents independently selected from halogen, CN, $NO_2$, $CF_3$, $R^4$, $OR^5$, $N(R^5)_2$, $CO_2R^5$, $COR^5$ and $CON(R^5)_2$;

$R^4$ represents $C_{1-6}$alkyl, $C_{3-7}$cycloalkyl, $C_{3-6}$cycloalkyl$C_{1-6}$alkyl, $C_{2-6}$alkenyl or $C_{2-6}$alkynyl, any of which may bear a substituent selected from halogen, CN, $NO_2$, $CF_3$, $OR^5$, $N(R^5)_2$, $CO_2R^5$, $COR^5$ and $CON(R^5)_2$; or $R^4$ represents Ar;

$R^5$ represents H or $C_{1-4}$alkyl which is optionally substituted with halogen, Ar, $CF_3$, OH, $C_{1-4}$alkoxy, $C_{1-4}$alkoxycarbonyl, amino, $C_{1-4}$alkylamino or di($C_{1-4}$alkyl)amino; and Ar represents phenyl or heteroaryl bearing 0-3 substituents selected from halogen, $C_{1-4}$alkyl, CN, $NO_2$, $CF_3$, OH, $C_{1-4}$alkoxy, $C_{1-4}$alkoxycarbonyl, amino, $C_{1-4}$alkylamino, di($C_{1-4}$alkyl)amino, carbamoyl, $C_{1-4}$alkylcarbamoyl and di($C_{1-4}$alkyl)carbamoyl;

or a pharmaceutically acceptable salt thereof.

In a subset of the compounds of formula I, $R^2$ and $R^3$ independently represent $C_{1-6}$alkyl, $C_{3-6}$cycloalkyl or $C_{3-6}$cycloalkyl$C_{1-6}$alkyl, any of which is optionally substituted with halogen, CN, $NO_2$, $CF_3$, Ar, $OR^5$, $N(R^5)_2$, $CO_2R^5$, $COR^5$ or $CON(R^5)_2$; or $R^2$ and $R^3$ complete a mono- or bicyclic heterocyclic ring system of 5-10 members, up to 2 of which are selected from N, O and S, including the nitrogen atom to which $R^2$ and $R^3$ are attached, said ring system optionally bearing up to 3 substituents independently selected from halogen, CN, $NO_2$, $CF_3$, $R^4$, $OR^5$, $N(R^5)_2$, $CO_2R^5$, $COR^5$ and $CON(R^5)_2$;

Where a variable occurs more than once in formula I or in a substituent thereof, the individual occurrences of that variable are independent of each other, unless otherwise specified.

As used herein, the expression "$C_{1-x}$alkyl" where x is an integer greater than 1 refers to straight-chained and branched alkyl groups wherein the number of constituent carbon atoms is in the range 1 to x. Particular alkyl groups include methyl, ethyl, n-propyl, isopropyl and t-butyl. Derived expressions such as "$C_{2-6}$alkenyl", "hydroxy$C_{1-6}$alkyl", "heteroaryl" $C_{1-16}$alkyl, "$C_{2-6}$alkynyl" and "$C_{1-6}$alkoxy" are to be construed in an analogous manner.

The expression "$C_{3-7}$cycloalkyl" as used herein refers to nonaromatic hydrocarbon ring systems comprising from 3 to 7 ring atoms. Examples include cyclopropyl, cyclobutyl, cyclopentyl, cyclohexyl, cyclohexenyl and cycloheptyl.

The expression "$C_{3-6}$ cycloalkyl$C_{1-6}$alkyl" as used herein includes cyclopropylmethyl, cyclobutylmethyl, cyclopentylmethyl and cyclohexylmethyl.

The expression "heteroaryl" as used herein means a cyclic or polycyclic system of up to 10 ring atoms selected from C, N, O and S, wherein at least one of the constituent rings is aromatic and wherein at least one atom in said ring is other than carbon. Preferably not more than 3 ring atoms are other than carbon. Where a heteroaryl ring comprises two or more atoms which are not carbon, not more than one of said atoms may be other than nitrogen. Examples of heteroaryl groups include pyridinyl, pyridazinyl, pyrimidinyl, pyrazinyl, pyrrolyl, furyl, thienyl, pyrazolyl, oxazolyl, isoxazolyl, thiazolyl, isothiazolyl, imidazolyl, triazolyl and the benzo-fused analogues thereof, oxadiazolyl, thiadiazolyl, tetrazolyl, and triazinyl.

The term "halogen" as used herein includes fluorine, chlorine, bromine and iodine, of which fluorine, chlorine and bromine are preferred.

For use in medicine, the compounds of formula I may advantageously be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Where the compounds according to the invention have at least one asymmetric center, they may accordingly exist as enantiomers. Where the compounds according to the invention possess two or more asymmetric centers, they may additionally exist as diastereoisomers. It is to be understood that all such isomers and mixtures thereof in any proportion are encompassed within the scope of the present invention.

In the compounds of formula I, n is 0 or 1, and bond a may be single or double, provided that bond a is single when n is 1. Thus, in a particular embodiment, bond a is single and n is 0. In an alternative embodiment, bond a is double and n is 0. In a third embodiment, bond a is single and n is 1. Preferably, n is 0.

$Ar^1$ represents optionally substituted phenyl, naphthyl or heteroaryl. Preferred substituents include halogens (especially bromine, chlorine and fluorine), $C_{1-6}$alkyl groups (especially methyl), OH and $OCH_2Ar$ (especially benzyloxy). If more than one substituent is present, preferably at least one of them is halogen.

A preferred heteroaryl embodiment of $Ar^1$ is optionally substituted thienyl, especially optionally substituted 2-thienyl.

Specific embodiments of $Ar^1$ include phenyl, 1-naphthyl, 3-methylphenyl, 4-methylphenyl, 3-bromophenyl, 2-chlorophenyl, 3-chlorophenyl, 4-chlorophenyl, 3,4-dichlorophenyl, 2,4,5-trichlorophenyl, 4-chloro-2,5-dimethylphenyl, 3-hydroxyphenyl, 3-benzyloxyphenyl, 4,5-dichlorothiophen-2-yl and 4,5-dibromothiophene-2-yl.

$R^1$ represents $C_{1-6}$alkyl (preferably $C_{1-4}$alkyl) such as methyl, $C_{2-6}$alkenyl (preferably $C_{2-4}$alkenyl) such as allyl, $C_{3-6}$cycloalkyl (preferably $C_{3-5}$cycloalkyl) such as cyclopropyl, or $C_{3-6}$cycloalkyl$C_{1-6}$alkyl such as cyclopropylmethyl. In a particular embodiment, $R^1$ represents methyl.

$R^2$ and $R^3$ independently represent H, $C_{1-6}$alkyl, $C_{3-6}$cycloalkyl or $C_{3-6}$cycloalkyl$C_{1-6}$alkyl groups, optionally substituted as defined previously, or $R^2$ and $R^3$ complete a 5-10 membered mono- or bicyclic heterocyclic ring system as defined previously. Preferably, $R^2$ and $R^3$ do not both represent H. Suitable $C_{1-6}$alkyl groups include methyl, ethyl, propyl and butyl, and suitable substituents include Ar, especially phenyl, and OAr, especially phenoxy. In a particular embodiment $R^2$ represents benzyl and $R^3$ represents methyl. In another particular embodiment, $R^2$ represents H and $R^3$ represents 2-phenoxyethyl. When $R^2$ and $R^3$ complete a heterocyclic ring system, said system may be mono- or bicyclic, and saturated or unsaturated. Bicyclic systems may be spiro-linked, ortho-fused or bridged. In the case of an ortho-fused system, the fused ring not containing the nitrogen atom bonded to $R^2$ and $R^3$ may be aromatic. Suitable heterocyclic ring systems include optionally substituted piperidine, piperazine, morpholine, thiomorpholine, tetrahydroquinoline, tetrahydroisoquinoline, decahydroquinoline, decahydroisoquinoline and tetrahydropyridine. Preferred substituents include $C_{1-6}$alkyl (especially methyl or t-butyl), $C_{3-7}$cycloalkyl (especially cyclohexyl), $OR^5$ (especially $C_{1-6}$alkoxy such as methoxy), $CO_2R^5$ (especially $C_{1-6}$alkoxycarbonyl such as ethoxycarbonyl), $CF_3$ and Ar (especially phenyl or methoxyphenyl).

Specific examples of N-heterocyclic groups completed by $R^2$ and $R^3$ include piperidin-1-yl, 4-methylpiperidin-1-yl, 4-t-butylpiperidin-1-yl, 4-trifluoromethylpiperidin-1-yl, 4-phenylpiperidin-1-yl, 4-(2-methoxyphenyl)piperazin-1-yl, 1,2,3,4-tetrahydroisoquinolin-2-yl, decahydroisoquinolin-2-yl and 4-phenyl-1,2,3,6-tetrahydropyridin-1-yl.

Further examples of N-heterocyclyl rings completed by $R^2$ and $R^3$ include 4-methyl-1,2,3,6-tetrahydropyridin-1-yl, 4,5-dimethyl-1,2,3,6-tetrahydropyridin-1-yl, 3-cyclohexylpiperidin-1-yl, 4-methoxypiperidin-1-yl and 3-(ethoxycarbonyl)piperidin-1-yl.

In the compounds of formula I, the $-NR^1SO_2Ar^1$ and $-NR^2R^3$ functionalities may be in either the cis or the trans configuration, but cis is preferred.

A preferred subclass of the compounds of the invention comprises the compounds of formula IA:

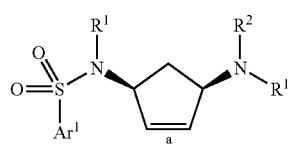

IA wherein bond a is single or double and $Ar^1$, $R^1$, $R^2$ and $R^3$ have the same definitions and preferred identities as before; and pharmaceutically acceptable salts thereof.

Specific compounds within the scope of the invention include:

cis-4,N-dimethyl-N-(3-(4-methylpiperidin-1-yl)cyclopentyl) -benzenesulfonamide hydrochloride;

cis-3,N-dimethyl-N-(3-(4-methylpiperidin-1-yl)cyclopentyl) -benzenesulfonamide hydrochloride;

cis-3-bromo-N-methyl-N-(3-(4-methylpiperidin-1-yl)cyclopentyl) -benzenesulfonamide hydrochloride;

cis-N-methyl-N-(3-(4-methylpiperidin-1-yl)cyclopentyl) -benzenesulfonamide hydrochloride;

cis-N-methyl-N-(3-(4-methylpiperidin-1-yl)cyclopentyl)-2, 4,5-trichlorobenzenesulfonamide hydrochloride;

cis-3,4-dichloro-N-methyl-N-(3-(4-methylpiperidin-1-yl) cyclopentyl) -benzenesulfonamide hydrochloride;

cis-4,5-dibromo-N-methyl-N-(3-(4-methylpiperidin-1-yl) cyclopentyl) -thiophene-2-sulfonamide hydrochloride;

cis-3-benzyloxy-N-methyl-N-(3-(4-methylpiperidin-1-yl) cyclopentyl) -benzenesulfonamide hydrochloride;

cis-N-methyl-N-(3-(4-methylpiperidin-1-yl)cyclopentyl) naphthalene -1-sulfonamide hydrochloride;

cis-2-chloro-N-methyl-N-(3-(4-methylpiperidin-1-yl)cyclopentyl) -benzenesulfonamide hydrochloride;

cis-3-chloro-N-methyl-N-(3-(4-methylpiperidin-1-yl)cyclopentyl) -benzenesulfonamide hydrochloride;

cis-4-chloro-N-methyl-N-(3-(4-methylpiperidin-1-yl)cyclopentyl) -benzenesulfonamide hydrochloride;

cis-3,5-dichloro-N-methyl-N-(3-(4-methylpiperidin-1-yl)
-cyclopentyl)benzenesulfonamide hydrochloride;
cis-4,5-dichloro-N-methyl-N-(3-(4-methylpiperidin-1-yl)
-cyclopentyl)thiophene-2-sulfonamide hydrochloride;
cis-4-chloro-2,5,N-trimethyl-N-(3-(4-methylpiperidin-1-yl)
-cyclopentyl)benzenesulfonamide hydrochloride;
cis-3,N-dimethyl-N-(3-(4-phenyl-1,2,5,6-tetrahydropyridin-
1-yl) -cyclopentyl)benzenesulfonamide hydrochloride;
cis-3,N-dimethyl-N-(3-(4-phenylpiperidin-1-yl)cyclopen-
tyl) -benzenesulfonamide hydrochloride;
cis-3-hydroxy-N-methyl-N-(3-(4-methylpiperidin-1-yl)cy-
clopentyl) -benzenesulfonamide hydrochloride;
trans-3,N-dimethyl-N-(3-(1,2,3,4-tetrahydroisoquinolin-2-
yl) -cyclopentyl)benzenesulfonamide hydrochloride;
cis-3,N-dimethyl-N-(3-(1,2,3,4-tetrahydroisoquinolin-2-yl)
-cyclopentyl)benzenesulfonamide hydrochloride;
cis-3,N-dimethyl-N-(3-(4-trifluoromethylpiperidin-1-yl)cy-
clopentyl) -benzenesulfonamide hydrochloride;
cis-3,N-dimethyl-N-(3-(4-tert-butylpiperidin-1-yl)cyclo-
pentyl) -benzenesulfonamide hydrochloride;
cis-N-benzyl-N,N'-dimethyl-N'-(3-methylbenzenesulfonyl)-
1,3-cyclopentanediamine hydrochloride;
(1R,3S)-cis-3,N-dimethyl-N-(3-(4-trifluoromethylpiperi-
din-1-yl) -cyclopentyl)benzenesulfonamide hydrochlo-
ride;
(1R,3S)-cis-4,5-dichloro-N-methyl-N-(3-(4-trifluorometh-
ylpiperidin-1-yl) -cyclopentyl)thiophene-2-sulfonamide
hydrochloride;
(1R,3S)-cis-4-chloro-2,5,N-trimethyl-N-(3-(4-trifluorom-
ethylpiperidin -1-yl)cyclopentyl)benzenesulfonamide
hydrochloride;
(1R,3S,4'aR,8'aS) or (1R,3S,4'aS,8'aR)cis-3,N-dimethyl-N-
(3-(decahydroisoquinolin-2-yl)cyclopentyl)benzene-
sulfonamide hydrochloride;
(1R,3S,4'aR,8'aS) or (1R,3S,4'aS,8'aR)-cis-4,5-dichloro-N-
methyl-N -(3-(decahydroisoquinolin-2-yl)cyclopentyl)
thiophene-2-sulfonamide hydrochloride;
cis-3,N-dimethyl-N-(4-(4-methylpiperidin-1-yl)cyclopent-
2-en-1-yl) -benzenesulfonamide hydrochloride;
(1S,4R)-cis-3,N-dimethyl-N-(4-(4-methylpiperidin-1-yl)cy-
clopent-2-en-1-yl)benzenesulfonamide hydrochloride and
(1S,4R)-cis-3,N-dimethyl-N-(4-(4-trifluoromethylpiperi-
din-1-yl) -cyclopent-2-en-1-yl)benzenesulfonamide
hydrochloride.
Further specific compounds of the invention include:
(1S,4R)-cis-3-chloro-N-methyl-N-(4-(4-methylpiperidin-1-
yl)cyclopent-2-en -1-yl)benzenesulfonamide hydrochlo-
ride;
(1S,4R)-cis-4,5-dichloro-N-methyl-N-(4-(4-methylpiperi-
din-1-yl)cyclopent -2-en-1-yl)thiophene-2-sulfonamide
hydrochloride;
(1S,4R)-cis-3,N-dimethyl-N-(4-(4-methyl-1,2,5,6-tetrahy-
dropyridin-1-yl)cyclopent-2-en-1-yl)benzenesulfonamide
hydrochloride;
(1S,4R)-cis-3,N-dimethyl-N-(4-(3,4-dimethyl-1,2,5,6-tet-
rahydropyridin-1-yl)cyclopent-2-en-1-yl)benzene-
sulfonamide hydrochloride;
(1S,4R,3'S)-cis-3,N-dimethyl-N-(4-(3-cyclohexylpiperidin-
1-yl)cyclopent-2-en-1-yl)benzenesulfonamide hydro-
chloride;
(1S,4R,3'R)-cis-3,N-dimethyl-N-(4-(3-cyclohexylpiperidin-
1-yl)cyclopent-2-en-1-yl)benzenesulfonamide hydro-
chloride;
(1S,4R)-cis-3,N-dimethyl-N-(4-(2-phenoxyethylamino)cy-
clopent-2-en-1-yl)benzenesulfonamide hydrochloride;

(1S,4R,3R)-cis-3,N-dimethyl-N-(4-(3-carboxyethylpiperi-
din-1-yl)cyclopent -2-en-1-yl)benzenesulfonamide
hydrochloride; and
1S,4R)-cis-3,N-dimethyl-N-(4-(4-methoxypiperidin-1-yl)
cyclopent-2-en-1-yl)benzenesulfonamide hydrochloride.

The invention also provides pharmaceutical compositions comprising one or more of the compounds according to this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Favoured unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of adverse conditions of the central nervous system such as depression or sleep disorders, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The invention further provides a compound of formula I as defined above, or a pharmaceutically acceptable salt thereof, for use in treatment of the human or animal body. Preferably, said treatment is for a condition which is susceptible to treatment by antagonism of the 5-HT$_7$ receptors, such as depression or a sleep disorder.

The invention further provides the use of a compound of formula I as defined above, or a pharmaceutically acceptable salt thereof, in the manufacture of a medicament for treatment or prevention of a condition which is susceptible to treatment by antagonism of the 5-HT$_7$ receptors, such as depression or a sleep disorder.

There is also disclosed a method of treating a subject suffering from or prone to a condition which is susceptible to treatment by antagonism of the 5-HT$_7$ receptors comprising administering to that subject a therapeutically effective amount of a compound of formula I or a pharmaceutically acceptable salt thereof. Preferably said condition is depression or a sleep disorder.

Compounds of formula I in which bond a is single may be prepared by reaction of an amine (1) with Ar$^1$SO$_2$Cl:

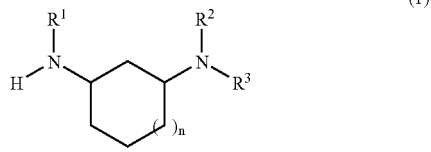
(1)

where n, Ar$^1$, R$^1$, R$^2$ and R$^3$ have the same meanings as before. The reaction is typically carried out in an aprotic solvent such as dichloromethane (DCM) in the presence of a tertiary amine such as triethylamine or aqueous sodium hydroxide at ambient temperature.

The amines (1) may be prepared by reaction of a protected aminocycloalkanone (2a) with R$^2$R$^3$NH and sodium triacetoxyborohydride, followed by deprotection of the amino group:

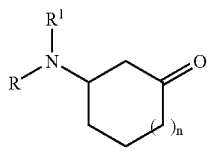

(2a) R = protecting group
(2b) R = H where n, Ar$^1$, R$^1$, R$^2$ and R$^3$ have the same meanings as before. The reductive alkylation may be carried out in dichloroethane at ambient temperature in the presence of acetic acid, while removal of the protecting group takes place under standard conditions. A preferred protecting group is t-butoxycarbonyl (Boc), which may be removed by treatment with acid, especially HCl in methanol.

The protected aminocycloalkanones (2a) are available from the addition of R$^1$NH$_2$ to the double bond of the appropriate 2-cycloalken-1-one, followed by protection of the resulting secondary amine (2b), where R$^1$ has the same meaning as before. The addition reaction is typically carried out in THF at reduced temperature (e.g. about 0° C.). Protection of the amine as the Boc derivative is typically carried out by treatment with di-t -butyldicarbonate in situ.

In a variation of this scheme, particularly suitable when n=1, PhCH$_2$OCONH$_2$ is added across the double bond of the 2-cycloalken-1-one, using (MeCN$_2$)PdCl$_2$ as catalyst (Gaunt and Spencer, Org. Lett. 2001, 3(1), 25), to give the 2-(benzyloxycarbonylamino)ketone. Reaction with R$^2$R$^3$NH and sodium triacetoxyborohydride as described above, followed by reduction of the benzyloxycarbonyl group with LiAlH$_4$, then provides (1) in which R$^1$ is methyl.

An alternative synthetic route to the compounds of formula I in which bond a is single involves reaction of a sulphonamido-cycloalkanone (3) with R$^2$R$^3$NH and sodium triacetoxyborohydride in the same manner as the conversion of (2a) to (1):

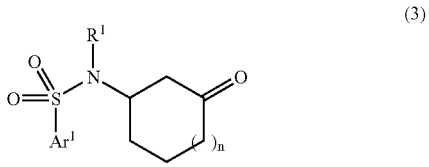
(3)

where n, Ar$^1$, R$^1$, R$^2$ and R$^3$ have the same meanings as before.

Sulphonamido-cycloalkanones (3) are available from the reaction of a secondary amine 2(b) with Ar$^1$SO$_2$Cl in the manner described previously for (1).

The reaction of R$^2$R$^3$NH with ketones (2a) to provide compounds (1), or with ketones (3) to provide compounds of formula I, typically gives a mixture of cis and trans isomers in roughly equal proportions. These may be separated by conventional means, such as chromatography or fractional crystallisation, in particular crystallisation after conversion to the corresponding hydrochloride salts.

An alternative route to the amines (1) in which n is 0 involves hydrogenation of aminocyclopentenes (4):

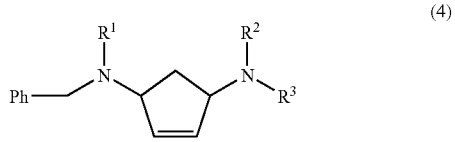
(4)

where R$^1$, R$^2$ and R$^3$ have the same meanings as before. The hydrogenation may be carried out over a Pd(OH)$_2$ catalyst. The aminocyclopentenes (4) are available from the reaction of cyclopentenyl esters (5) with PhCH$_2$NHR$^1$:

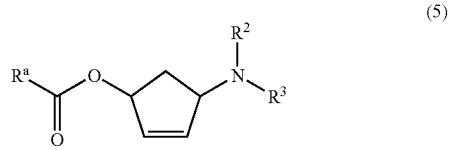
(5)

where R$^a$ represents C$_{1-6}$alkyl (such as methyl), phenyl or substituted phenyl (e.g. 2,4-dichlorophenyl) and R$^2$ and R$^3$ have the same meanings as before. The reaction takes place at ambient temperature in THF in the presence of tris(dibenzylideneacetone)dipalladium(0), triphenylphosphine and triethylamine.

The esters (5) are available from the acylation of the alcohols (6) with R$^a$COCl, and the alcohols (6) are prepared by reaction of acetates (7) with R$^2$R$^3$NH:

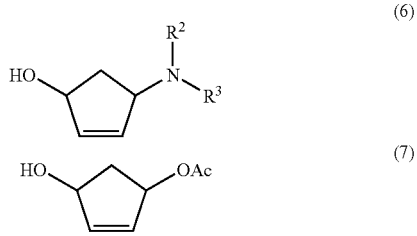

where R$^a$, R$^2$ and R$^3$ have the same meanings as before. The conversion of (7) to (6) occurs under the same conditions as the conversion of (5) to (4).

Compounds of formula I in which n is 0 and bond a is double may be prepared by reaction of compounds (6) with [Ar$^1$SO$_2$NR$^1$]—Na$^+$, where R$^1$ and Ar$^1$ have the same meanings as before. The sodium salt is prepared from the corresponding sulphonamide by treatment with NaH, while the reaction with (6) takes place in the presence of tris(dibenzylideneacetone)dipalladium(0) (Pd$_2$ dba$_3$), triphenylphosphine and 1,2-bis(diphenylphosphino)ethane (dppe) in THF/DMSO.

Alternatively, compound (7) may be treated with an aroyl chloride (e.g. 2,4-dichlorobenzoyl chloride), and the resulting ester reacted with [Ar$^1$SO$_2$NR$^1$]—Na$^+$ to provide a sulphonamide (8):

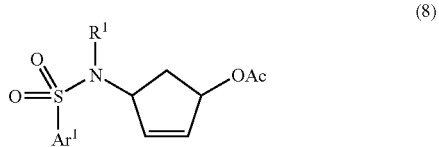

where Ar$^1$ and R$^1$ have the same meanings as before. The reaction takes place in DMF at ambient temperature in the presence of tetrakis(triphenylphosphine)palladium(0) and dppe. Subsequent treatment of compounds (8) with R$^2$R$^3$NH provides compounds of formula I in which n is 0 and bond a is double, the reaction taking place at about 50° C. in DMF in the presence of Pd$_2$ dba$_3$, dppe and triethylamine.

The stereochemistry of the starting material (7) is preserved in the transformations described above, and so by starting with enantiomerically-pure (7), it is possible to obtain enantiomerically-pure product of formula I.

It will be appreciated that any compound of formula I initially obtained from any of the above processes may, where appropriate, subsequently be elaborated into a further desired compound of formula I using techniques known from the art.

Where the above-described processes for the preparation of the compounds of use in the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds of use in the invention.

EXAMPLE 1 cis-4,N-Dimethyl-N-(3-(4-methylpiperidin-1-yl)cyclopentyl)-benzenesulfonamide hydrochloride Step 1. 3-[(tert-Butyloxycarbonyl)methylamino]cyclopentan-1-one Methylamine (2.0M in THF; 40 ml, 80 mmol) was added dropwise over 5 minutes to a solution of 2-cyclopenten-1-one (6.8 ml, 81 mmol) in dichloromethane (70 ml) cooled to −4° C. The resulting mixture was stirred at −4° C. to +1° C. for 1 h 30 min. then treated with di-tert-butyl dicarbonate (17.81 g, 81.6 mmol) in dichloromethane (25 ml). The reaction mixture was stirred at 0° C. for 15 min., allowed to warm to room temperature over 30 min. then stirred overnight (20 h). The mixture was concentrated in vacuo and the residue purified by flash chromatography, eluting with 1:3 then 1:2 ethyl acetate-isohexane, to give the title compound (7.78 g, 45%) as an pale amber oil; $\delta_H$ (400 MHz, CDCl$_3$) 1.47 (9H, s), 1.93-2.04 (1H, m), 2.14-2.31 (3H, m), 2.37-2.47 (2H, m), 2.80 (3H, s), 4.71 (1H, br s).

Step 2. cis-1-[(tert-Butyloxycarbonyl)methylamino]-3-(4-methylpiperidin-1-yl)cyclopentane hydrochloride Sodium triacetoxyborohydride (3.37 g, 15.9 mmol) was added to a solution of 3-[(tert-butyloxycarbonyl)methylamino]cyclopentan-1-one (2.42 g, 11.3 mmol), 4-methylpiperidine (1.2 ml, 10 mmol) and acetic acid (0.65 ml, 11 mmol) in 1,2-dichloroethane (40 ml). The resulting mixture was stirred at room temperature overnight (22 h). 1M Aqueous sodium hydroxide (100 ml) was added and the mixture extracted with dichloromethane (2×40 ml). The combined extracts were dried (MgSO$_4$) and evaporated. The residue was dissolved in diethyl ether (40 ml) and treated with 1M hydrogen chloride in diethyl ether (10 ml, 10 mmol) to give a precipitate. The solid was collected under suction, washed with diethyl ether then isohexane and dried in vacuo (2.89 g). A portion of this solid (1.764 g) was recrystallized from methanol-ethyl acetate to afford the title product (0.7203 g, 35%) as a white solid; $\delta_H$ (400 MHz, CD$_3$OD) 1.02 (3H, d, J 6.7 Hz), 1.39-1.41 (2H, m), 1.46 (9H, s), 1.71 (1H, m), 1.83-1.98 (6H, m), 2.14 (1H, m), 2.27 (1H, m), 2.82 (3H, s), 2.93 (2H, m), 3.50 (1H, m), 3.59 (2H, m), 4.44 (1H, m); m/z (ES$^+$) 297 ([M+H]$^+$), 241 (100%).

Step 3. cis-1-Methylamino-3-(4-methylpiperidin-1-yl)cyclopentane dihydrochloride cis-1-[(tert-Butyloxycarbonyl)methylamino]-3-(4-methylpiperidin-1-yl)cyclopentane hydrochloride (394.5 mg, 1.19 mmol) was dissolved in hydrogen chloride in methanol [prepared by cautious addition of acetyl chloride (2 ml) to methanol (20 ml)]. The resulting solution was stirred at room temperature for 3 hours, concentrated in vacuo to give an oil which was crystalized from methanol-ethyl acetate. The solid was collected under suction, washed with ethyl acetate and dried in vacuo to give the title compound (295.3 mg, 93%) as a white solid; $\delta_H$ (400 MHz, CD$_3$OD) 1.02 (3H, d, J 6.4 Hz), 1.51-1.63 (2H, m), 1.73 (1H, m), 1.92-2.29 (7H, m), 2.67 (1H, m), 2.73 (3H, s), 2.98 (2H, m), 3.62 (4H, m); m/z (ES$^+$) 197 ([M+H]$^+$, 100%), 166.

Step 4. cis-4,N-Dimethyl-N-(3-(4-methylpiperidin-1-yl)cyclopentyl)-benzenesulfonamide hydrochloride A mixture of cis-1-methylamino-3-(4-methylpiperidin-1-yl)cyclopentane dihydrochloride (24.5 mg, 0.091 mmol) and 4-toluenesulfonyl chloride (27.9 mg, 0.146 mmol) in dichloromethane (2 ml) and 1M aqueous sodium hydroxide (2 ml) was rapidly stirred at room temperature overnight (22 hours). The phases were separated and the aqueous extracted with more dichloromethane (5 ml). The combined organics were dried (MgSO$_4$) and evaporated. The residue was dissolved in methanol-ethyl acetate and treated with excess 1M hydrogen chloride in diethyl ether. Recrystallization of the resulting solid from methanol-ethyl acetate gave the title compound (31.5 mg, 89%) as a white solid; $\delta_H$ (400 MHz, CD$_3$OD) 1.00 (3H, d, J 6.1 Hz), 1.43 (2H, m), 1.62-1.83 (5H, m), 1.91 (2H, m), 2.04-2.18 (2H, m), 2.43 (3H, s), 2.77 (3H, s), 2.89 (2H, m), 3.50 (3H, m), 4.41 (1H, m), 7.40 (2H, d, J 8.5 Hz), 7.71 (2H, d, J 8.5 Hz); m/z (ES$^+$) 351 ([M+H]$^+$, 100%).

Prepared in an analogous manner were Examples 2-16:

EXAMPLE 2 cis-3,N-Dimethyl-N-(3-(4-methylpiperidin-1-yl)cyclopentyl)-benzenesulfonamide hydrochloride $\delta_H$ (400 MHz, CD$_3$OD) 1.00 (3H, d, J 6.1 Hz), 1.40 (2H, m), 1.63-1.82 (5H, m), 1.91 (2H, m), 2.05-2.17 (2H, m), 2.44 (3H, s), 2.78 (3H, s), 2.89 (2H, m), 3.49 (3H, m), 4.42 (1H, m), 7.47 (2H, m), 7.63 (2H, m); m/z (ES$^+$) 351 ([M+H]$^+$, 100%).

EXAMPLE 3 cis-3-Bromo-N-methyl-N-(3-(4-methylpiperidin-1-yl)cyclopentyl)-benzenesulfonamide hydrochloride $\delta_H$ (400 MHz, CD$_3$OD) 1.00 (3H, d, J 6.4 Hz), 1.43 (2H, m), 1.65-1.84 (5H, m), 1.92 (2H, m), 2.07-2.20 (2H, m), 2.81 (3H, s), 2.90 (2H, m), 3.51 (3H, m), 4.45 (1H, m), 7.52 (1H, t, J 8.0 Hz), 7.82 (2H, m), 7.98 (1H, m); m/z (ES$^+$) 415/417 ([M+H]$^+$, 100%).

EXAMPLE 4 cis-N-Methyl-N-(3-(4-methylpiperidin-1-yl)cyclopentyl)-benzenesulfonamide hydrochloride $\delta_H$ (400 MHz, CD$_3$OD) 1.00 (3H, d, J 6.4 Hz), 1.43 (2H, m), 1.67 (3H, m), 1.78 (2H, m), 1.91 (2H, m), 2.05-2.17 (2H, m), 2.80 (3H, s), 2.89 (2H, m), 3.48 (2H, m), 3.55 (1H, m), 4.43 (1H, m), 7.59 (2H, m), 7.66 (1H, m), 7.84 (2H, m); m/z (ES$^+$) 337 ([M+H]$^+$, 100%).

EXAMPLE 5 cis-N-Methyl-N-(3-(4-methylpiperidin-1-yl)cyclopentyl)-2,4,5-trichlorobenzenesulfonamide hydrochloride $\delta_H$ (400 MHz, CD$_3$OD) 1.01 (3H, d, J 6.1 Hz), 1.44 (2H, m), 1.69 (1H, m), 1.82-1.97 (6H, m), 2.13 (1H, m), 2.24 (1H, m), 2.89 (2H, m), 2.92 (3H, s), 3.48 (1H, m), 3.56 (2H, m), 4.37 (1H, m), 7.89 (1H, d, J 1.2 Hz), 8.20 (1H, d, J 1.2 Hz); m/z (ES$^+$) 439/441/443 ([M+H]$^+$).

EXAMPLE 6 cis-3,4-Dichloro-N-methyl-N-(3-(4-methylpiperidin-1-yl)cyclopentyl)-benzenesulfonamide hydrochloride $\delta_H$ (400 MHz, CD$_3$OD) 1.00 (3H, d, J 6.1 Hz), 1.43 (2H, m), 1.69-1.84 (5H, m), 1.92 (2H, m), 2.09-2.21 (2H, m), 2.82 (3H, s), 2.90 (2H, m), 3.52 (3H, m), 4.45 (1H, m), 7.76 (2H, m), 7.99 (1H, m); m/z (ES$^+$) 405/407/409 ([M+H]$^+$).

EXAMPLE 7 cis-4,5-Dibromo-N-methyl-N-(3-(4-methylpiperidin-1-yl)cyclopentyl)-thiophene-2-sulfonamide hydrochloride $\delta_H$ (400 MHz, CD$_3$OD) 1.01 (3H, d, J 6.4 Hz), 1.44 (2H, m), 1.66-1.94 (7H, m), 2.13 (1H, m), 2.24 (1H, m), 2.86 (3H, s), 2.92 (2H, m), 3.45-3.59 (3H, m), 4.41 (1H, m), 7.58 (1H, s); m/z (ES$^+$) 501 ([M+H]$^+$, 100%).

EXAMPLE 8 cis-3-Benzyloxy-N-methyl-N-(3-(4-methylpiperidin-1-yl)cyclopentyl)-benzenesulfonamide hydrochloride $\delta_H$ (400 MHz, CD$_3$OD) 1.00 (3H, d, J 6.4 Hz), 1.43 (2H, m), 1.57 (2H, q, J 8.1 Hz), 1.73 (3H, m), 1.91 (2H, m), 2.02-2.14 (2H, m), 2.72 (3H, s), 2.88 (2H, m), 3.39-3.55 (3H, m), 4.35 (1H, m), 5.19 (2H, s), 7.29-7.52 (9H, m); m/z (ES$^+$) 443 ([M+H]$^+$, 100%).

EXAMPLE 9 cis-N-Methyl-N-(3-(4-methylpiperidin-1-yl)cyclopentyl)naphthalene-1-sulfonamide hydrochloride $\delta_H$ (400 MHz, CD$_3$OD) 0.99 (3H, d, J 6.0 Hz), 1.42 (2H, m), 1.64-1.92 (7H, m), 2.06-2.18 (2H, m), 2.84 (3H, s), 2.88 (2H, m), 3.50 (3H, m), 4.50 (1H, m), 7.60-7.71 (3H, m), 8.03 (1H, m), 8.19 (1H, m), 8.23 (1H, m), 8.61 (1H, m); m/z (ES$^+$) 387 ([M+H]$^+$, 100%).

EXAMPLE 10 cis-2-Chloro-N-methyl-N-(3-(4-methylpiperidin-1-yl)cyclopentyl)-benzenesulfonamide hydrochloride $\delta_H$ (400 MHz, CD$_3$OD) 1.01 (3H, d, J 6.4 Hz), 1.43 (2H, m), 1.69 (1H, m), 1.78-1.95 (6H, m), 2.13 (1H, m), 2.24 (1H, m), 2.88 (3H, s), 2.93 (2H, m), 3.53 (3H, m), 4.39 (1H, m), 7.50 (1H, m), 7.61 (2H, m), 8.09 (1H, m); m/z (ES$^+$) 371/373 ([M+H]$^+$).

EXAMPLE 11 cis-3-Chloro-N-methyl-N-(3-(4-methylpiperidin-1-yl)cyclopentyl)-benzenesulfonamide hydrochloride $\delta_H$ (400 MHz, CD$_3$OD) 1.00 (3H, d, J 6.1 Hz), 1.39 (2H, m), 1.65-1.82 (5H, m), 1.92 (2H, m), 2.09-2.20 (2H, m), 2.81 (3H, s), 2.90 (2H, m), 3.53 (3H, m), 4.45 (1H, m), 7.59 (1H, t, J 8.0 Hz), 7.68 (1H, m), 7.77 (1H, m), 7.84 (1H, m); m/z (ES$^+$) 371/373 ([M+H]$^+$).

EXAMPLE 12 cis-4-Chloro-N-methyl-N-(3-(4-methylpiperidin-1-yl)cyclopentyl)-benzenesulfonamide hydrochloride $\delta_H$ (400 MHz, CD$_3$OD) 1.00 (3H, d, J 6.3 Hz), 1.40 (2H, m), 1.65-1.81 (5H, m), 1.92 (2H, m), 2.06-2.19 (2H, m), 2.80 (3H, s), 2.89 (2H, m), 3.51 (3H, m), 4.43 (1H, m), 7.61 (2H, m), 7.82 (2H, m); m/z (ES$^+$) 371/373 ([M+H]$^+$).

EXAMPLE 13 cis-3,5-Dichloro-N-methyl-N-(3-(4-methylpiperidin-1-yl)cyclopentyl)-benzenesulfonamide hydrochloride $\delta_H$ (400 MHz, CD$_3$OD) 1.01 (3H, d, J 6.3 Hz), 1.42 (2H, m), 1.65-1.85 (5H, m), 1.93 (2H, m), 2.12-2.20 (2H, m), 2.84 (3H, s), 2.91 (2H, m), 3.53 (3H, m), 4.46 (1H, m), 7.79 (3H, m); m/z (ES$^+$) 405/407/409 ([M+H]$^+$).

EXAMPLE 14 cis-4,5-Dichloro-N-methyl-N-(3-(4-methylpiperidin-1-yl)cyclopentyl)-thiophene-2-sulfonamide hydrochloride $\delta_H$ (400 MHz, CD$_3$OD) 1.01 (3H, d, J 6.3 Hz), 1.41 (2H, m), 1.66-1.86 (5H, m), 1.93 (2H, m), 2.13 (1H, m), 2.25 (1H, m), 2.86 (3H, s), 2.91 (2H, m), 3.52 (3H, m), 4.41 (1H, m), 7.60 (1H, s); m/z (ES$^+$) 411/413/415 ([M+H]$^+$).

EXAMPLE 15 cis-4-Chloro-2,5,N-trimethyl-N-(3-(4-methylpiperidin-1-yl)cyclopentyl)-benzenesulfonamide hydrochloride $\delta_H$ (360 MHz, CD$_3$OD) 1.01 (3H, d, J 6.3 Hz), 1.43 (2H, m), 1.69 (1H, m), 1.81-1.94 (6H, m), 2.13 (1H, m), 2.23 (1H, m), 2.40 (3H, m), 2.51 (3H, s), 2.80 (3H, s), 2.91 (2H, m), 3.52 (3H, m), 4.29 (1H, m), 7.42 (1H, s), 7.83 (1H, s); m/z (ES$^+$) 399/401 ([M+H]$^+$).

EXAMPLE 16 cis-3,N-Dimethyl-N-(3-(4-phenyl-1,2,5,6-tetrahydropyridin-1-yl)-cyclopentyl)benzenesulfonamide hydrochloride $\delta_H$ (400 MHz, CD$_3$OD) 1.70 (2H, m), 1.84 (2H, m), 2.20 (2H, m), 2.44 (3H, s), 2.81 (3H, s), 2.88 (2H, br s), 3.66 (1H, m), 3.90 (4H, v br s), 4.47 (1H, m), 6.11 (1H, br s), 7.30-7.39 (3H, m), 7.47 (4H, m), 7.65 (2H, m); m/z (ES$^+$) 411 ([M+H]$^+$, 100%).

EXAMPLE 17 cis-3 N-Dimethyl-N-(3-(4-phenylpiperidin-1-yl) cyclopentyl)-benzenesulfonamide hydrochloride cis-3,N-Dimethyl-N-(3-(4-phenyl-1,2,5,6-tetrahydropyridin-1-yl)cyclopentyl)benzenesulfonamide hydrochloride (Example 16) (60.6 mg, 0.136 mmol) in methanol (10 ml) was hydrogenated over 20% palladium hydroxide on carbon (19.6 mg) at 45 psi for 2.5 hours. The mixture was filtered and concentrated in vacuo. Recrystallization from methanol-ethyl acetate gave the title compound (40.5 mg, 67%) as a white solid; $\delta_H$ (400 MHz, CD$_3$OD) 1.69 (2H, m), 1.83 (2H, m), 1.99 (2H, m), 2.09-2.21 (4H, m), 2.44 (3H, s), 2.81 (3H, s), 2.88 (1H, m), 3.07 (2H, m), 3.54 (1H, m), 3.62 (1H, m), 3.69 (1H, m), 4.45 (1H, m), 7.24 (3H, m), 7.32 (2H, m), 7.48 (2H, m), 7.64 (2H, m); m/z (ES$^+$) 413 ([M+H]$^+$, 100%).

EXAMPLE 18 cis-3-Hydroxy-N-methyl-N-(3-(4-methylpiperidin-1-yl)cyclopentyl)-benzenesulfonamide hydrochloride cis-3-Benzyloxy-N-methyl-N-(3-(4-methylpiperidin-1-yl)cyclopentyl)benzenesulfonamide hydrochloride (Example 8) (64.7 mg, 0.135 mmol) in methanol (10 ml) was hydrogenated over 20% palladium hydroxide on carbon (38 mg) at 45 psi for 3.5 hours. The mixture was filtered and concentrated in vacuo. Recrystallization from methanol-ethyl acetate gave the title compound (47.3 mg, 90%) as a white solid; $\delta_H$ (400 MHz, CD$_3$OD) 1.00 (3H, d, J 6.4 Hz), 1.44 (2H, m), 1.65-1.82 (5H, m), 1.91 (2H, m), 2.07-2.08 (2H, m), 2.79 (3H, s), 2.90 (2H, m), 3.50 (3H, m), 4.40 (1H, m), 7.04 (1H, m), 7.19 (1H, t, J 2.0 Hz), 7.26 (1H, m), 7.39 (1H, t, J 8.0 Hz); m/z (ES$^+$) 353 ([M+H]$^+$, 100%).

EXAMPLE 19 trans-3,N-Dimethyl-N-(3-(1,2,3,4-tetrahydroisoquinolin-2-yl)cyclopentyl)-benzenesulfonamide hydrochloride and cis-3,N-dimethyl-N-(3-(1,2,3,4-tetrahydroisoquinolin-2-yl)cyclopentyl)benzenesulfonamide hydrochloride Step 1. cis/trans-1-Methylamino-3-(3-(1,2,3,4-tetrahydroisoquinolin-2-yl)cyclopentane Dihydrochloride Sodium triacetoxyborohydride (237 mg, 1.12 mmol) was added to a solution of 3-[(tert-butyloxycarbonyl)methylamino]cyclopentan-1-one [Example 1, step 1] (214.3 mg, 1.00 mmol), 1,2,3,4-tetrahydroisoquinoline (120 µl, 0.98 mmol) and acetic acid (46 µl, 0.80 mmol) in 1,2-dichloroethane (5 ml). The resulting mixture was stirred at room temperature overnight (20 h). 1M Aqueous sodium hydroxide (25 ml) was added and the mixture extracted with dichloromethane (25 ml then 10 ml). The combined extracts were dried (MgSO$_4$), evaporated and the residue purified by medium pressure silica chromatography, eluting with 5% methanol in dichloromethane, to give a yellow oil (288.2 mg). This oil was dissolved in a solution of hydrogen chloride in methanol [prepared by cautious addition of acetyl chloride (1 ml) to methanol (10 ml)] and the resulting solution stirred at room temperature for 4.5 h. The reaction mixture was concentrated in vacuo to give the title compound (266.6 mg, 87%) as a foam; m/z (ES$^+$) 231 ([M+H]$^+$, 100%).

Step 2. trans-3,N-Dimethyl-N-(3-(1,2,3,4-tetrahydroisoquinolin-2-yl)cyclopentyl)benzenesulfonamide hydrochloride and cis-3,N-dimethyl-N -(3-(1,2,3,4-tetrahydroisoquinolin-2-yl)cyclopentyl)benzenesulfonamide hydrochloride A mixture of cis/trans-1-methylamino-3-(3-(1,2,3,4-tetrahydroisoquinolin-2-yl)cyclopentane dihydrochloride (139.6 mg, 0.46 mmol), triethylamine (250 μl, 1.8 mmol), 4-dimethylaminopyridine (6.3 mg, 0.05 mmol) and 3-toluenesulfonyl chloride (91.8 mg, 0.48 mmol) in dichloromethane (10 ml) was stirred at room temperature overnight (18 h). The reaction mixture was poured into 1M aqueous sodium hydroxide (20 ml), the phases separated and the aqueous extracted with more dichloromethane (10 ml). The combined organics were dried (MgSO$_4$) and evaporated. The residue was purified by medium pressure silica chromatography, eluting with 5% methanol in dichloromethane, to afford trans-3,N-dimethyl-N-(3-(1,2,3,4-tetrahydroisoquinolin-2-yl)cyclopentyl)benzenesulfonamide (55.6 mg, 31%) as the first eluted isomer followed by cis-3,N-dimethyl-N-(3-(1,2,3,4-tetrahydroisoquinolin-2-yl) cyclopentyl)benzenesulfonamide (41.2 mg, 23%). The hydrochloride salts were prepared by treating ethyl acetate solutions with hydrogen chloride in diethyl ether. trans-3,N-Dimethyl-N-(3-(1,2,3,4-tetrahydroisoquinolin-2-yl)cyclopentyl) -benzenesulfonamide hydrochloride; δ$_H$ (400 MHz, CD$_3$OD) 1.60-1.86 (3H, m), 2.02-2.16 (2H, m), 2.30 (1H, m), 2.44 (3H, s), 2.77 (3H, s), 3.18 (2H, br s), 3.55 (2H, v br s), 3.77 (1H, m), 4.42 (2H, br s), 4.60 (1H, m), 7.21 (1H, m), 7.25-7.33 (3H, m), 7.48 (2H, m), 7.65 (2H, m); m/z (ES$^+$) 385 ([M+H]$^+$, 100%). cis-3,N-Dimethyl-N-(3-(1,2,3,4-tetrahydroisoquinolin-2-yl)cyclopentyl) -benzenesulfonamide hydrochloride; δ$_H$ (400 MHz, CD$_3$OD) 1.72 (2H, m), 1.89 (2H, m), 2.17-2.31 (2H, m), 2.44 (3H, s), 2.81 (3H, s), 3.19 (2H, br s), 3.5 (2H, v br s), 3.71 (1H, m), 4.4 (2H, v br s), 4.47 (1H, m), 7.20 (1H, m), 7.28 (3H, m), 7.47 (2H, m), 7.65 (2H, m); m/z (ES$^+$) 385 ([M+H]$^+$, 100%).

EXAMPLE 20 cis-3,N-Dimethyl-N-(3-(4-trifluoromethylpiperidin-1-yl)cyclopentyl) -benzenesulfonamide hydrochloride Step 1. 3-((3,N-Dimethyl)benzenesulfonamido)cyclopentan-1-one Methylamine (2.0M in THF; 10 ml, 20 mmol) was added dropwise over 5 minutes to a solution of 2-cyclopenten-1-one (1.68 ml, 20 mmol) in dichloromethane (16 ml) cooled to −4° C. The resulting mixture was stirred at −4° C. to +1° C. for 1 hour 30 minutes then added to a solution of 3-toluenesulfonyl chloride (3.83 g, 20.1 mmol), triethylamine (2.8 ml, 20 mmol) and 4-dimethylaminopyridine (128.4 mg, 1.05 mmol) in dichloromethane (50 ml). The reaction mixture was stirred at 0° C. for 30 minutes, allowed to warm to room temperature over 30 minutes then stirred for a further 2 hours. The mixture was poured into 1M hydrochloric acid (100 ml), separated and the organic phase washed with saturated aqueous sodium hydrogen carbonate (100 ml). The organic phase was dried (MgSO$_4$), concentrated in vacuo and the residue purified by flash chromatography, eluting with 1:3, 1:2 then 1:1 ethyl acetate-isohexane, to give the title compound (2.48 g, 46%) as an pale amber oil; δ$_H$ (400 MHz, CDCl$_3$) 1.89 (1H, m), 2.05 (1H, m), 2.10-2.22 (3H, m), 2.34 (1H, m), 2.44 (3H, s), 2.78 (3H, s), 4.60 (1H, m), 7.40 (2H, m), 7.60 (2H, m).

Step 2. cis-3,N-Dimethyl-N-(3-(4-trifluoromethylpiperidin-1-yl) -cyclopentyl)benzenesulfonamide hydrochloride Sodium triacetoxyborohydride (340.4 mg, 1.61 mmol) was added to a solution of 3-((3,N-dimethyl)benzenesulfonamido)cyclopentan-1-one (280.7 mg, 1.05 mmol), and 4-trifluoromethylpiperidine (194.8 mg, 1.27 mmol) in 1,2-dichloroethane (10 ml). The resulting mixture was stirred at room temperature overnight (20 hours). 1M Aqueous sodium hydroxide (25 ml) was added and the mixture extracted with dichloromethane (2×10 ml). The combined extracts were dried (K$_2$CO$_3$) and evaporated. The residue was purified by medium pressure silica chromatography, eluting with 2.5% methanol in dichloromethane, to afford cis-3,N-dimethyl-N-(3-(4-trifluoromethylpiperidin-1-yl)cyclopentyl) -benzenesulfonamide (93.1 mg, 22%). A portion of this material was dissolved in ethyl acetate, warmed and treated with hydrogen chloride in diethyl ether to afford the title compound as a white crystalline solid; δ$_H$ (400 MHz, CD$_3$OD) 1.68 (2H, m), 1.83 (4H, m), 2.06-2.18 (4H, m), 2.44 (3H, s), 2.60 (1H, m), 2.79 (3H, s), 2.99 (2H, m), 3.51 (1H, m), 3.63 (1H, m), 3.69 (1H, m), 4.43 (1H, m), 7.47 (2H, m), 7.63 (2H, m); m/z (ES$^+$) 405 ([M+H]$^+$, 100%).

Prepared in an analogous manner to Example 20 were the following two examples:

EXAMPLE 21 cis-3,N-Dimethyl-N-(3-(4-tert-butylpiperidin-1-yl) cyclopentyl) -benzenesulfonamide hydrochloride δ$_H$ (400 MHz, CD$_3$OD) 0.91 (9H, s), 1.36 (1H, m), 1.53 (2H, m), 1.66 (2H, m), 1.77 (2H, m), 1.97 (2H, m), 2.05-2.18 (2H, m), 2.44 (3H, s), 2.79 (3H, s), 2.86 (2H, m), 3.44 (1H, m), 3.54 (1H, m), 3.61 (1H, m), 4.42 (1H, m), 7.47 (2H, m), 7.63 (2H, m); m/z (ES$^+$) 393 ([M+H]$^+$, 100%).

EXAMPLE 22 cis-N-Benzyl-N,N'-dimethyl-N'-(3-methylbenzenesulfonyl)-1,3-cyclopentanediamine hydrochloride δ$_H$ (400 MHz, CD$_3$OD) 1.71 (2H, m), 1.92 (2H, m), 2.10-2.28 (2H, br m), 2.44 (3H, s), 2.67 (3H, s), 2.82 (3H, s), 3.67 (1H, m), 4.09 (1H, m), 4.44 (1H, m), 4.49 (1H, m), 7.49 (7H, m), 7.65 (2H, m); m/z (ES$^+$) 373 ([M+H]$^+$, 100%).

EXAMPLE 23

(1R,3S)cis-3,N-Dimethyl-N-(3-(4-trifluoromethylpiperidin-1-yl)-cyclopentyl)benzenesulfonamide hydrochloride

Step 1. (1S,4R)-cis-4-(4-trifluoromethylpiperidin-1-yl)-2-cyclopenten-1-ol

A solution of tris(dibenzylideneacetone)dipalladium(0) (38.2 mg, 0.042 mmol) and triphenylphosphine (72.6 mg, 0.277 mmol) in tetrahydrofuran (15 ml) was stirred at room temperature for 60 minutes. This solution was then added to a mixture of (1S,4R)-cis-4-acetoxy-2-cyclopenten-1-ol (224.8 mg, 1.58 mmol), 4-trifluoromethylpiperidine (475.4 mg, 3.10 mmol) and triethylamine (0.49 ml, 3.5 mmol). The resulting mixture was stirred at room temperature overnight (16 hours), filtered and the filtrate evaporated. Diethyl ether (50 ml) was added to the residue and the mixture extracted with 1M hydrochloric acid (2×10 ml). The acid extracts were combined, diluted with diethyl ether (20 ml) and cautiously basified with potassium carbonate. The phases were separated and the aqueous phase extracted with more diethyl ether (20 ml). The combined organics were dried ($K_2CO_3$) and evaporated to afford the title compound (306.5 mg, 82%) as a waxy solid; $\delta_H$ (400 MHz, $CDCl_3$) 1.56-1.69 (3H, m), 1.87 (2H, m), 2.00 (1H, m), 2.10 (2H, m), 2.39 (1H, dt, J 14.1, 7.4 Hz), 2.94 (1H, br d, J 12 Hz), 3.04 (1H, br d, J 12 Hz), 3.61 (1H, m), 4.72 (1H, m), 5.98 (2H, m); m/z ($ES^+$) 236 ($[M+H]^+$, 100%), 218.

Step 2. (1S,4R)-cis-1-((2,4-Dichloro)benzoyloxy)-4-(4-trifluoromethylpiperidin-1-yl)-2-cyclopentene 2,4-Dichlorobenzoyl chloride (0.27 ml, 1.9 mmol) was added to a solution of (1S,4R)cis-4-(4-trifluoromethylpiperidin-1-yl)-2-cyclopenten-1-ol (298.8 mg, 1.27 mmol) and pyridine (0.31 ml, 3.8 mmol) in dichloromethane (10 ml) at −5° C. The resulting mixture was stirred at −5° C. for 10 minutes, the cooling bath removed and the mixture stirred at room temperature overnight. The reaction mixture was washed with saturated sodium hydrogen carbonate (2×20 ml) and the aqueous washes back extracted with dichloromethane (2×10 ml). The combined organics were dried ($K_2CO_3$), concentrated and the residue purified by flash chromatography eluting with 1:3 then 1:1 ethyl acetate-isohexane to give the title compound (436.8 mg, 84%); $\delta_H$ (360 MHz, $CDCl_3$) 1.55-1.69 (2H, m), 1.84-1.90 (3H, m), 1.99 (1H, m), 2.10-2.19 (2H, m), 2.56 (1H, dt, J 14.5, 8 Hz), 2.90 (1H, br d, J 11.8 Hz), 3.01 (1H, br d, J 11.8 Hz), 3.84 (1H, dt, 1.9, 5.0 Hz), 5.81 (1H, m), 6.06 (1H, m), 6.13 (1H, m), 7.30 (1H, dd, J 8.4, 2.0 Hz), 7.47 (1H, d, J 2.0 Hz), 7.77 (1H, d, J 8.4 Hz); m/z ($ES^+$) 408/410/412 ($[M+H]^+$).

Step 3. (1S,4R)-cis-1-(N-Benzyl)methylamino-4-(4-trifluoromethylpiperidin-1-yl)-2-cyclopentene A solution of tris(dibenzylideneacetone)dipalladium(0) (22.5 mg, 0.025 mmol) and triphenylphosphine (39.4 mg, 0.150 mmol) in tetrahydrofuran (8 ml) was stirred at room temperature for 30 minutes. This solution was then added to a solution of (1S,4R)-cis-1-((2,4-dichloro)benzoyloxy)-4-(4-trifluoromethylpiperidin-1-yl)-2-cyclopentene (393.8 mg, 0.965 mmol), N-benzylmethylamine (0.25 ml, 1.94 mmol) and triethylamine (0.30 ml, 2.15 mmol) in tetrahydrofuran (2 ml) at 0° C. The resulting solution was stirred at 0° C. for 10 minutes then at room temperature for 3 hours. The reaction mixture was concentrated in vacuo, taken up in diethyl ether (20 ml) and extracted with 1M hydrochloric acid (2×10 ml). The aqueous extracts were washed with diethyl ether (20 ml), combined, diluted with diethyl ether (20 ml) and cautiously basified with potassium carbonate. The phases were separated and the aqueous extracted with more diethyl ether (20 ml). The combined organics were dried ($K_2CO_3$) and evaporated to give the title compound (282.1 mg, 86%) as an amber oil; $\delta_H$ (400 MHz, $CDCl_3$) 1.65 (2H, m), 1.75 (1H, dt, J 12.8, 7.6 Hz), 1.87 (2H, m), 1.96-2.08 (2H, m), 2.15 (2H, m), 2.19 (3H, s), 2.93 (1H, br d, J 11 Hz), 3.05 (1H, br d, J 11 Hz), 3.46 (1H, d, J 13.1 Hz), 3.60 (1H, d, J 13.1 Hz), 3.67 (1H, m), 3.81 (1H, m), 5.91 (1H, m), 5.97 (1H, m), 7.24 (1H, m), 7.32 (4H, m); m/z ($ES^+$) 339 ($[M+H]^+$, 100%), 249, 218.

Step 4. (1R,3S)-cis-1-Methylamino-3-(4-trifluoromethylpiperidin-1-yl)-cyclopentane dihydrochloride (1S,4R)-cis-1-(N-Benzyl)methylamino-4-(4-trifluoromethylpiperidin-1-yl)-2-cyclopentene (272.4 mg, 0.805 mmol) was dissolved in methanol (10 ml) and treated with 1M hydrogen chloride in diethyl ether (2.0 ml, 2.0 mmol). The resulting solution was hydrogenated over 20% palladium hydroxide on carbon (53.4 mg) at 50 psi overnight (18 hours). The mixture was filtered and concentrated in vacuo. Recrystallisation from methanol-ethyl acetate gave the title compound (207.5 mg, 80%) as an off-white solid; $\delta_H$ (400 MHz, $CD_3OD$) 1.96-2.29 (9H, m), 2.62 (1H, m), 2.70 (1H, dt, J 13.1, 7.2 Hz), 2.73 (3H, s), 3.07 (2H, m), 3.64 (2H, m), 3.75 (2H, m); m/z ($ES^+$) 251 ($[M+H]^+$, 100%).

Step 5. (1R,3S)-cis-3,N-Dimethyl-N-(3-(4-trifluoromethylpiperidin-1-yl)-cyclopentyl)benzenesulfonamide hydrochloride A mixture of (1R,3S)cis-1-methylamino-3-(4-trifluoromethylpiperidin-1-yl)cyclopentane dihydrochloride (25.8 mg, 0.080 mmol) and 3-toluenesulfonyl chloride (18.2 mg, 0.095 mmol) in dichloromethane (2 ml) and 1M aqueous sodium hydroxide (2 ml) was rapidly stirred at room temperature overnight (24 hours). The phases were separated and the aqueous extracted with more dichloromethane (5 ml). The combined organics were dried ($K_2CO_3$) and evaporated. The residue was dissolved in methanol-ethyl acetate and treated with 1M hydrogen chloride in diethyl ether (0.10 ml). The solvent was evaporated and the residual solid recrystallised from methanol-ethyl acetate to give the title compound (31.0 mg, 88%) as a white solid; $[\alpha]_D$+9.0° (c 0.29, MeOH); $\delta_H$ (400 MHz, $CD_3OD$) 1.68 (2H, m), 1.83 (4H, m), 2.06-2.18 (4H, m), 2.44 (3H, s), 2.60 (1H, m), 2.79 (3H, S), 2.99 (2H, m), 3.51 (1H, m), 3.63 (1H, m), 3.69 (1H, m), 4.43 (1H, m), 7.47 (2H, m), 7.63 (2H, m); m/z ($ES^+$) 405 ($[M+H]^+$, 100%).

Prepared in an analogous manner to Example 23 were the following two examples:

EXAMPLE 24

(1R,3S)-cis-4,5-Dichloro-N-methyl-N-(3-(4-trifluoromethylpiperidin-1-yl)-cyclopentyl)thiophene-2-sulfonamide hydrochloride $\delta_H$ (400 MHz, $CD_3OD$) 1.78-1.92 (6H, m), 2.16 (3H, m), 2.27 (1H, m), 2.65 (1H, m), 2.88 (3H, s), 3.01 (2H, m), 3.54 (1H, m), 3.70 (2H, m), 4.43 (1H, m), 7.61 (1H, s); m/z ($ES^+$) 465/467/469 ($[M+H]^+$).

EXAMPLE 25

(1R,3S)-cis-4-Chloro-2,5,N-trimethyl-N-(3-(4-trifluoromethylpiperidin-1-yl)cyclopentyl)benzenesulfonamide hydrochloride $\delta_H$ (400 MHz, CD$_3$OD) 1.80-1.96 (6H, m), 2.13-2.25 (4H, m), 2.40 (3H, s), 2.51 (3H, s), 2.61 (1H, m), 2.81 (3H, s), 3.00 (2H, m), 3.53 (1H, m), 3.70 (2H, m), 4.30 (1H, m), 7.42 (1H, s), 7.83 (1H, s); m/z (ES$^+$) 453/455 ([M+H]$^+$).

EXAMPLE 26

(1R,3S,4'aR,8'aS) or (1R,3S,4'aS,8'aR)-cis-3,N-Dimethyl-N-(3-(decahydroisoquinolin-2-yl)cyclopentyl)benzenesulfonamide hydrochloride Step 1. (1S,4R,4'aR,8'aS) or (1S,4R,4'aS,8'aR)-cis-4-(decahydroisoquinolin-2-yl)-2-cyclopenten-1-ol A solution of tris(dibenzylideneacetone)dipalladium(0) (81.0 mg, 0.088 mmol) and triphenylphosphine (140.2 mg, 0.535 mmol) in tetrahydrofuran (20 ml) was stirred at room temperature for 30 minutes. This solution was then added to a mixture of (1S,4R)-cis-4-acetoxy-2-cyclopenten-1-ol (509.7 mg, 3.59 mmol), (±)-trans-decahydroisoquinoline (1.01 g, 7.25 mmol) and triethylamine (1.2 ml, 8.6 mmol). The resulting mixture was stirred at room temperature overnight (16 hours) then evaporated. Diethyl ether (50 ml) was added to the residue and the mixture extracted with 1M hydrochloric acid (2×10 ml). The acid extracts were combined, diluted with diethyl ether (20 ml) and cautiously basified with potassium carbonate. The phases were separated and the aqueous phase extracted with more diethyl ether (20 ml). The combined organics were dried (K$_2$CO$_3$) and evaporated to afford an amber oil (0.9987 g). This oil began to crystallise on standing overnight. Isohexane (10 ml) was added, swirled to dissolve the oil and allowed to stand for 10 minutes. The crystalline solid present was collected under suction, washed with isohexane and dried in vacuo to afford the title compound (162.7 mg, 21%) [single diastereoisomer of undetermined absolute stereochemistry of the trans-decahydroisoquinoline portion]; $\delta_H$ (400 MHz, CDCl$_3$) 0.83-1.03 (3H, m), 1.14-1.34 (4H, m), 1.51-1.78 (7H, m), 2.10 (1H, m), 2.37 (1H, dt, J 13.7, 7.4 Hz), 2.69 (1H, ddd, J 10.6, 3.5, 2.0 Hz), 2.96 (1H, m), 3.53 (1H, m), 4.69 (1H, m), 5.95 (1H, dt, J 5.5, 2.0 Hz), 6.00 (1H, m); m/z (ES$^+$) 222 ([M+H]$^+$, 100%).

Step 2. (1R,3S,4'aR,8'aS) or (1R,3S,4'aS,8'aR)-cis-3,N-Dimethyl-N-(3-(decahydroisoquinolin-2-yl)cyclopentyl)benzenesulfonamide hydrochloride (1S,4R,4'aR,8'aS) or (1S,4R,4'aS,8'aR)-cis-4-(decahydroisoquinolin-2-yl)-2-cyclopenten-1-ol was further functionalised as in Example 23, steps 2-5 [replacing (1S,4R)-cis-4-(4-trifluoromethylpiperidin-1-yl)-2-cyclopenten-1-ol] to afford the title compound; $\delta_H$ (400 MHz, CD$_3$OD) 0.98-1.08 (2H, m), 1.19-1.87 (5H, m), 1.62-1.87 (9H, m), 2.05-2.20 (2H, m), 2.44 (3H, s), 2.64 (1H, t, J 12.0 Hz), 2.79 (3H, s), 2.89 (1H, m), 3.32 (1H, m), 3.47 (1H, m), 3.57 (1H, m), 4.42 (1H, m), 7.47 (2H, m), 7.61-7.65 (2H, m); m/z (ES$^+$) 391 ([M+H]$^+$, 100%).

Prepared in an analogous manner was the following example:

EXAMPLE 27

(1R,3S,4'aR,8'aS) or (1R,3S,4'aS,8'aR)-cis-4,5-Dichloro-N-methyl-N -(3-(decahydroisoquinolin-2-yl)cyclopentyl)thiophene-2-sulfonamide hydrochloride $\delta_H$ (400 MHz, CD$_3$OD) 0.99-1.09 (2H, m), 1.20-1.55 (5H, m), 1.65-1.92 (9H, m), 2.13 (1H, m), 2.26 (1H, m), 2.66 (1H, t, J 12 Hz), 2.87 (3H, s), 2.91 (1H, m), 3.37 (1H, m), 3.50 (1H, m), 3.59 (1H, m), 4.41 (1H, m), 7.60 (1H, s); m/z (ES$^+$) 451/453/455 ([M+H]$^+$).

EXAMPLE 28 cis-3,N-Dimethyl-N-(4-(4-methylpiperidin-1-yl) cyclopent-2-en-1-yl)-benzenesulfonamide hydrochloride A solution of tris(dibenzylideneacetone)dipalladium(0) (35.0 mg, 0.038 mmol) and triphenylphosphine (60.3 mg, 0.23 mmol) in tetrahydrofuran (5 ml) was stirred at room temperature for 50 minutes. This solution was then added to a mixture of cis-3,5-diacetoxs-1-cyclopentene (0.25 ml, 1.53 mmol), 4-methylpiperidine (0.22 ml, 1.86 mmol) and triethylamine (0.47 ml, 3.37 mmol) at 0° C. The resulting solution was stirred at 0° C. for 15 minutes and then at room temperature overnight (16 hours). More 4-methylpiperidine (0.18 ml) was added and the mixture stirred at 50° C. (oil bath temperature) overnight (16 hours). The reaction mixture was concentrated in vacuo, diethyl ether added (10 ml) and the mixture extracted with 1M hydrochloric acid (2×10 ml). The acid extracts were combined, diluted with diethyl ether (20 ml) and cautiously basified with potassium carbonate. The phases were separated and the aqueous phase extracted with more diethyl ether (2×10 ml). The combined organics were dried (K$_2$CO$_3$) and evaporated to an oil (171.7 mg). The bulk of this material (165.8 mg) was dissolved in tetrahydrofuran (6 ml) and added to a mixture of the sodium salt of 3,N-dimethylbenzenesulfonamide (162.0 mg, 0.80 mmol) and 1,2-bis(diphenylphoshino)ethane (15.1 mg, 0.038 mmol) in DMSO (2 ml). To this was added a solution of tris(dibenzylideneacetone)dipalladium(0) (16.8 mg, 0.018 mmol) and triphenylphosphine (32.0 mg, 0.122 mmol) in tetrahydrofuran (2 ml) that had been aged as above. The resulting mixture was stirred at 50° C. (oil bath temperature) for 5 hours. The reaction mixture was allowed to cool to room temperature, diluted with water (100 ml) and 4M sodium hydroxide (20 ml) and extracted with ethyl acetate (2×50 ml). The combined extracts were dried (K$_2$CO$_3$), evaporated and purified by medium pressure silica chromatography, eluting with 4% methanol in dichloromethane. The purified product was dissolved in methanol-ethyl acetate and treated with excess 1M hydrogen chloride in diethyl ether. Recrystallisation of the resulting solid from methanol-ethyl acetate gave the title compound (37.1 mg, 6%); $\delta_H$ (400 MHz, CD$_3$OD) 1.00 (3H, d, J 6.4 Hz), 1.42 (2H, m), 1.70 (1H, m), 1.79 (1H, m), 1.93 (2H, m), 2.45 (3H, s), 2.56 (1H, dt, J 13.7, 7.9 Hz), 2.73 (3H, s), 2.91 (1H, m), 3.02 (1H, m), 3.37 (1H, m), 3.56 (1H, m), 4.22 (1H, m), 5.12 (1H, m), 5.82 (1H, m), 6.10 (1H, m), 7.50 (2H, m), 7.67 (2H, m); m/z (ES$^+$) 349 ([M+H]$^+$, 100%).

EXAMPLE 29

(1S,4R)-cis-3,N-Dimethyl-N-(4-(4-methylpiperidin-1-yl)cyclopent-2-en-1-yl)benzenesulfonamide hydrochloride Step 1. (1S,4R)-cis-1-((2,4-Dichloro)benzoyloxy)-4-(4-methylpiperidin-1-yl) -2-cyclopentene A solution of tris(dibenzylideneacetone)dipalladium(0) (33.8 mg, 0.037 mmol) and triphenylphosphine (59.4 mg, 0.226 mmol) in tetrahydrofuran (8 ml) was stirred at room temperature for 60 minutes. This solution was then added to a solution of (1S,4R)-cis-4-acetoxy-2-cyclopenten-1-ol (22.2 mg, 1.77 mmol), 4-methylpiperidine (0.42 ml, 3.55 mmol) and triethylamine (0.54 ml, 3.87 mmol) in tetrahydrofuran (5 ml). The resulting solution was stirred at room temperature overnight (16 hours), filtered and the filtrate evaporated. Diethyl ether (50 ml) was added to the residue and the mixture extracted with 1M hydrochloric acid (2×10 ml). The acid extracts were combined, diluted with diethyl ether (20 ml) and cautiously basified with potassium carbonate. The phases were separated and the aqueous phase extracted with more diethyl ether (20 ml). The combined organics were dried (K$_2$CO$_3$) and evaporated to afford an amber oil (275.6 mg). This oil was dissolved in dichloromethane (10 ml) and pyridine (0.5 ml) and cooled to 0° C. 2,4-Dichlorobenzoyl chloride (0.43 ml, 3.1 mmol) was added and the resulting mixture stirred at 0° C. for 10 minutes, the cooling bath removed and the mixture stirred at room temperature overnight. The reaction mixture was concentrated in vacuo, the residue treated with 1M aqueous sodium hydroxide (25 ml) and extracted with ethyl acetate (2×25 ml). The extracts were washed with saturated aqueous sodium chloride (25 ml). The combined organic were dried (K$_2$CO$_3$), concentrated and the residue purified by flash chromatography eluting with 5% then 7.5% methanol in dichloromethane to give the title compound (421.2 mg, 78%); δ$_H$ (400 MHz, CDCl$_3$) 0.93 (3H, d, J 6.2 Hz), 1.23-1.38 (3H, m), 1.66 (2H, br d, J 12 Hz), 1.92 (1H, dt, J 14.5, 4.7 Hz), 2.16 (2H, m), 2.56 (1H, dt, J 14.5, 8.0 Hz), 2.80 (1H, br d, J 12.4 Hz), 2.92 (1H, br d, J 12.3 Hz), 3.83 (1H, m), 5.81 (1H, m), 6.03 (1H, m), 6.18 (1H, m), 7.30 (1H, dd, J 8.3, 2.0 Hz), 7.47 (1H, d, J 2.0 Hz), 7.77 (1H, d, J 8.3 Hz); m/z (ES$^+$) 354/356/358 ([M+H]$^+$).

Step 2. (1S,4R)-cis-3,N-Dimethyl-N-(4-(4-methylpiperidin-1-yl)cyclopent -2-en-1-yl)benzenesulfonamide hydrochloride Tetrakis(triphenylphoshine)palladium(0) (16.6 mg, 0.014 mmol) was added to a mixture of (1S,4R)-cis-1-((2,4-dichloro)benzoyloxy)-4-(4-methylpiperidin-1-yl)-2-cyclopentene (100.0 mg, 0.282 mmol), the sodium salt of 3,N-dimethylbenzenesulfonamide (126.5 mg, 0.626 mmol) and 1,2-bis(diphenylphoshino)ethane (5.6 mg, 0.014 mmol) in tetrahydrofuran (4 ml) and DMSO (1 ml). The resulting mixture was stirred at room temperature for 4.5 hours, concentrated in vacuo and treated with 1M aqueous sodium hydroxide (25 ml). The mixture was extracted with ethyl acetate (2×25 ml), the combined extracts dried (K$_2$CO$_3$), evaporated and the residue purified by medium pressure silica chromatography, eluting with 4% methanol in dichloromethane, to give (1S,4R)-cis-3,N-dimethyl-N-(4-(4-methylpiperidin-1-yl)cyclopent-2-en-1-yl)benzenesulfonamide (35.0 mg, 36%). This material was dissolved in ethyl acetate, warmed and treated with hydrogen chloride in diethyl ether to afford the title compound (25.5 mg) as a crystalline solid; δ$_H$ (400 MHz, CD$_3$OD) 1.00 (3H, d, J 6.4 Hz), 1.42 (2H, m), 1.70 (1H, m), 1.79 (1H, m), 1.93 (2H, m), 2.45 (3H, s), 2.56 (1H, dt, J 13.7, 7.9 Hz), 2.73 (3H, s), 2.91 (1H, m), 3.02 (1H, m), 3.37 (1H, m), 3.56 (1H, m), 4.22 (1H, m), 5.12 (1H, m), 5.82 (1H, m), 6.10 (1H, m), 7.50 (2H, m), 7.67 (2H, m); m/z (ES$^+$) 349 ([M+H]$^+$, 100%).

Prepared in an analogous manner to Example 29 were the following two examples:

EXAMPLE 30

(1S,4R)-cis-3-Chloro-N-methyl-N-(4-(4-methylpiperidin-1-yl)cyclopent-2-en-1-yl)benzenesulfonamide hydrochloride δ$_H$ (400 MHz, CD$_3$OD) 1.00 (3H, d, J 6.3 Hz), 1.42 (2H, m), 1.70 (1H, m), 1.80 (1H, m), 1.94 (2H, m), 2.58 (1H, m), 2.76 (3H, s), 2.92 (1H, m), 3.03 (1H, m), 3.37 (1H, m), 3.56 (1H, m), 4.23 (1H, m), 5.15 (1H, m), 5.88 (1H, m), 6.12 (1H, m), 7.62 (1H, m), 7.70 (1H, m), 7.81 (1H, m), 7.88 (1H, m); m/z (ES$^+$) 369/371 ([M+H]$^+$).

EXAMPLE 31

(1S,4R)-cis-4,5-Dichloro-N-methyl-N-(4-(4-methylpiperidin-1-yl)cyclopent -2-en-1-yl)thiophene-2-sulfonamide hydrochloride δ$_H$ (400 MHz, CDCl$_3$) 1.01 (3H, d, J 6.4 Hz), 1.42 (2H, m), 1.72 (1H, m), 1.87 (1H, m), 1.96 (2H, m), 2.66 (1H, m), 2.81 (3H, s), 2.95 (1H, m), 3.05 (1H, m), 3.41 (1H, br d, J 12 Hz), 3.58 (1H, br d, J 12 Hz), 4.26 (1H, m), 5.12 (1H, m), 6.01 (1H, m), 6.17 (1H, m), 7.65 (1H, s); m/z (ES$^+$) 409/411/413 ([M+H]$^+$).

EXAMPLE 32

(1S,4R)-cis-3,N-Dimethyl-N-(4-(4-trifluoromethylpiperidin-1-yl)cyclopent -2-en-1-yl)benzenesulfonamide hydrochloride Step 1. (1S,4R)-cis-3,N-Dimethyl-N-((4-hydroxy)cyclopent-2-en-1-yl)benzenesulfonamide Sodium hydride, 60% dispersion in oil (0.31 g, 7.7 mmol) was added portionwise to a solution of 3,N-dimethylbenzenesulfonamide (1.30 g, 7.02 mmol) in tetrahydrofuran (40 ml) and the resulting suspension stirred at room temperature for 15 minutes. The mixture was diluted with DMSO (10 ml) and treated with of (1R,4S)-cis-4-acetoxy-2-cyclopenten-1-ol (0.49 g), 1,2-bis(diphenylphoshino)ethane (69.3 mg, 0.174 mmol) and tetrakis(triphenylphosphine)palladium(0) (199.0 mg, 0.172 mmol). The reaction mixture was stirred at 50° C. (oil bath temperature) overnight (24 hours), allowed to cool, poured into water (750 ml) and extracted with ethyl acetate (2×250 ml). The extracts were washed with saturated aqueous sodium chloride (250 ml), combined, dried (MgSO$_4$) and evaporated. The residue was purified by flash chromatography, eluting with 1:1, 2:1 and finally 3:1 ethyl acetate-isohexane to give the title compound (149.9 mg, 16%) as a yellow oil; δ$_H$ (400 MHz, CDCl$_3$) 1.28 (1H, dt, J 14.5, 4.7 Hz), 1.71 (1H, d, J 5.4 Hz), 2.40-2.48 (4H, m), 2.67 (3H, s), 4.68 (1H, m), 4.99 (1H, m), 5.54 (1H, m), 5.93 (1H, m), 7.40 (2H, m), 7.60-7.63 (2H, m).

Step 2. (1S,4R)-cis-3,N-Dimethyl-N-(4-(4-trifluoromethylpiperidin-1-yl)-cyclopent-2-en-1-yl)benzenesulfonamide hydrochloride 2,4-Dichlorobenzoyl chloride (0.10 ml, 0.71 mmol) was added to a solution of (1S,4R)-cis-3,N-dimethyl-N-((4-hydroxy)cyclopent-2-en-1-yl)-benzenesulfonamide (146.4 mg, 0.548 mmol) and pyridine (0.22 ml, 2.7 mmol) in dichloromethane (5 ml) at 0° C. The resulting mixture was stirred at 0° C. for 5 minutes, the cooling bath removed and the mixture stirred at room temperature for 4 hours. The reaction mixture was concentrated in vacuo, the residue treated with 1M hydrochloric acid (10 ml) and extracted with ethyl acetate (2×10 ml). The extracts were washed with 1M hydrochloric acid (10 ml) and saturated aqueous sodium hydrogen carbonate (2×10 ml), combined, dried (MgSO$_4$) and evaporated give a yellow oil (229.4 mg). This oil, 4-trifluoromethylpiperidine (203.1 mg, 1.3 mmol) and triethylamine (0.175 ml, 1.3 mmol) were dissolved in tetrahydrofuran (4 ml). To this mixture was added a solution of tris(dibenzylideneacetone)dipalladium(0) (13.0 mg, 0.014 mmol) and triphenylphosphine (22.7 mg, 0.087 mmol) in tetrahydrofuran (5 ml) that had been aged for 40 minutes. The resulting mixture was stirred at room temperature overnight, concentrated in vacuo and the residue purified by flash chromatography, eluting with 1:3, 1:2 then 1:1 ethyl acetate-isohexane to give (1S,4R)-cis-3,N-dimethyl-N-(4-(4-trifluoromethylpiperidin-1-yl)cyclopent-2-en-1-yl)benzenesulfonamide (73.3 mg, 35%). This material was dissolved in ethyl acetate, warmed and treated with hydrogen chloride in diethyl ether to afford, on cooling, the title compound (54.3 mg) as a white crystalline solid; $\delta_H$ (400 MHz, CD$_3$OD) 1.78-1.88 (3H, m), 2.19 (2H, br d, J 13.5 Hz), 2.45 (3H, s), 2.59 (2H, m), 2.73 (3H, s), 3.00 (1H, m), 3.11 (1H, m), 3.52 (1H, m), 3.70 (1H, m), 4.28 (1H, m), 5.13 (1H, m), 5.86 (1H, m), 6.10 (1H, m), 7.50 (2H, m), 7.65-7.69 (2H, m); m/z (ES$^+$) 403 ([M+H]$^+$, 100%).

EXAMPLE 33

(1S,4R)-cis-3,N-Dimethyl-N-(4-(4-methyl-1,2,5,6-tetrahydropyridin-1-yl)cyclopent-2-en-1-yl)benzenesulfonamide hydrochloride

Step 1. (1S,4R)-cis-1-((2,4-Dichloro)benzoyloxy)-4-acetoxy-2-cyclopentene

A solution of (1S,4R)-cis-4-acetoxy-2-cyclopenten-1-ol (1.0 g, 7 mmol) and pyridine (3.2 ml, 40 mmol) in dichloromethane (50 ml) was cooled in an ice bath and 2,4-dichlorobenzoyl chloride added dropwise. The resultant solution was allowed to stir to room temperature over 2 hrs then concentrated in vacuo. The residue was suspended in ethyl acetate (100 ml) and washed with 1N aqueous hydrochloric acid (100 ml), followed by aqueous sodium bicarbonate solution (100 ml). The organic solution was dried (MgSO$_4$), concentrated and the residue purified by flash chromatography eluting with 10% then 25% ethyl acetate in iso-hexane to give the title compound (2.18 g, 99%); $\delta_H$ (360 MHz, CDCl$_3$) 1.91 (1H, dt, J 3.8, 15 Hz), 2.06 (3H, s), 2.98 (1H, dt, J 7.5, 15 Hz), 5.59-5.62 (1H, m), 5.77-5.81 (1H, m), 6.16-6.22 (2H, m), 7.29 (1H, dd, J 2.0, 8.4 Hz), 7.48 (1H, d, J 2.0 Hz), 7.79 (1H, d, J 8.4 Hz).

Step 2. (1S,4R)cis-3,N-Dimethyl-N-(4-acetoxycyclopent-2-en-1-yl) benzenesulfonamide A solution of 3,N-dimethylbenzenesulfonamide (300 mg, 1.6 mmol) in N,N-dimethylformamide (10 ml) was treated with 60% sodium hydride in mineral oil (68 mg, 1.7 mmol) and stirred at room temperature for 20 minutes. Tetrakistriphenylphosphinepalladium(0) (114 mg, 0.1 mmol) was then added along with 1,2-bis(diphenylphosphino)ethane (42 mg). The solution was degassed with nitrogen and a solution of (1S,4R)cis-1-((2,4-dichloro)benzoyloxy)-4-acetoxy-2-cyclopentene in N,N-dimethylformamide (10 ml) was added. The solution formed was stirred at ambient temperature for 2 hours, then diluted with ethyl acetate (100 ml). The organics were washed with water (2×100 ml) and dried (MgSO$_4$) before being concentrated in vacuo. The residue was purified by flash chromatography eluting with 10% then 25% ethyl acetate in iso-hexane to give the title compound (396 mg, 80%); $\delta_H$ (360 MHz, CDCl$_3$) 1.37 (1H, dt, J 4.2, 15 Hz), 1.99 (3H, s), 2.43 (3H, s), 2.50 (1H, dt, J 8.2, 15 Hz), 2.63 (3H, s), 5.04-5.06 (1H, m), 5.45-5.48 (1H, m), 5.62-5.65 (1H, m), 5.93-5.96 (1H, m), 7.39-7.41 (2H, m), 7.60-7.63 (2H, m).

Step 3. (1S,4R)-cis-3,N-Dimethyl-N-(4-(4-methyl-1,2,5,6-tetrahydropyridin-1-yl)cyclopent-2-en-1-yl) benzenesulfonamide hydrochloride Tris(dibenzylideneacetone)dipalladium(0) (32 mg, 0.03 mmol) and 1,2-bis(diphenylphosphino)ethane (28 mg, 0.07 mmol) were dissolved in N,N-dimethylformamide (2 ml) and stirred at ambient temperature for 30 minutes. (1S,4R)-cis-3,N-Dimethyl-N-(4-acetoxycyclopent-2-en-1-yl)benzenesulfonamide (100 mg, 0.32 mmol) and 4-methyl-1,2,5,6-tetrahydropyridine hydrochloride (94 mg, 0.7 mmol) were dissolved in N,N-dimethylformamide (3 ml) and treated with triethylamine (0.24 ml, 1.7 mmol). This solution was added to the aged catalyst mixture and the combined solution heated at 50° C. for 16 hours. After cooling, the mixture was diluted with ethyl acetate (50 ml) and washed with water (2×50 ml). The organics were dried (MgSO$_4$) and concentrated, and the residue purified by flash chromatography eluting with 5% methanol in dichloromethane to give (1S,4R)-cis-3,N-dimethyl-N-(4-(4-methyl-1,2,5,6-tetrahydropyridin-1-yl)cyclopent-2-en-1-yl)benzenesulfonamide as a gum. This gum was dissolved in ethyl acetate (10 ml) and treated with 1M ethereal hydrogen chloride (1 ml). The solid formed was removed by filtration and recrystallised from methanol/diethyl ether to give the title compound as a white solid (25 mg, 22%); $\delta_H$ (360 MHz, CD$_3$OD) 1.74-1.82 (4H, m), 2.36-2.40 (2H, m), 2.44 (3H, s), 2.56-2.64 (1H, m), 2.72 (3H, s) 3.50-3.72 (4H, m), 4.31 (1H, br m), 5.13 (1H, br m), 5.45 (1H, br m), 5.84 (1H, br m), 6.11 (1H, br m), 7.46-7.50 (2H, m), 7.65-7.68 (2H, m); m/z (ES$^+$) 347 ([M+H]$^+$).

Prepared in an analogous manner were the following:

EXAMPLE 34

(1S,4R)-cis-3 N-Dimethyl-N-(4-(3,4-dimethyl-1,2,5,6-tetrahydropyridin-1-yl)cyclopent-2-en-1-yl)benzenesulfonamide hydrochloride $\delta_H$ (360 MHz, CD$_3$OD) 1.68 (3H, s), 1.73 (3H, s), 1.79-1.85 (1H, m), 2.27-2.40 (2H, m) 2.44 (3H, s), 2.58-2.66 (1H, m), 2.73 (3H, s), 3.10-3.24 (1H, m), 3.52-3.68 (3H, m), 4.29-4.33 (1H, m), 5.11-5.15 (1H, m), 5.83-584 (1H, m), 6.12-6.13 (1H, m), 7.47-7.50 (2H, m), 7.65-7.68 (2H, m); m/z (ES$^+$) 361 ([M+H]$^+$).

EXAMPLE 35

(1S,4R,3'S)-cis-3,N-Dimethyl-N-(4-(3-cyclohexylpiperidin-1-yl)cyclopent-2-en-1-yl)benzenesulfonamide hydrochloride and (1S,4R,3'R)-cis-3,N-dimethyl-N-(4-(3-cyclohexylpiperidin-1-yl)cyclopent-2-en-1-yl)benzenesulfonamide hydrochloride Diastereomer A:
$\delta_H$ (360 MHz, CD$_3$OD) 1.05-1.28 (8H, m), 1.58-1.80 (9H, m), 1.86-1.90 (1H, m), 1.98-2.02 (1H, m), 2.44 (3H, s), 2.55-2.59 (1H, m), 2.72 (3H, s), 2.74-2.78 (1H, m), 3.49-3.53 (1H, m), 4.22 (1H, m), 5.08-5.12 (1H, m), 5.83-5.84 (1H, m), 6.10-6.11 (1H, m), 7.49-7.50 (2H, m), 7.65-7.69 (2H, m); m/z (ES$^+$) 417 ([M+H]$^+$).

Diastereomer B:
$\delta_H$ (360 MHz, CD$_3$OD) 1.03-1.31 (7H, m), 1.60-1.90 (9H, m), 1.97-2.01 (1H, m), 2.44 (3H, s), 2.52-2.70 (2H, m), 2.72 (3H, s), 2.87 (1H, m), 3.47-3.50 (1H, m), 4.22 (1H, m), 5.08-5.12 (1H, m), 5.81-5.82 (1H, m), 6.09-6.11 (1H, m), 7.49-7.50 (2H, m), 7.65-7.68 (2H, m); m/z (ES$^+$) 417 ([M+H]$^+$).

EXAMPLE 36

(1S,4R)-cis-3,N-Dimethyl-N-(4-(2-phenoxyethylamino)cyclopent-2-en-1-yl)benzenesulfonamide hydrochloride $\delta_H$ (400 MHz, CD$_3$OD) 1.62 (1H, dt, J 7.6, 15 Hz), 2.44 (3H, s), 2.64 (1H, dt, J 8.0, 15 Hz) 2.73 (3H, s), 3.42-3.52 (2H, m), 4.23-4.30 (3H, m), 5.14-5.17 (1H, m), 5.80-5.83 (1H, m), 6.04-6.06 (1H, m), 6.97-7.01 (3H, m), 7.28-7.32 (2H, m), 7.48-7.49 (2H, m), 7.64-7.68 (2H, m); m/z (ES$^+$) 387 ([M+H]$^+$).

EXAMPLE 37

(1S,4R,3'R)-cis-3,N-Dimethyl-N-(4-(3-carboxyethylpiperidin-1-yl)cyclopent-2-en-1-yl)benzenesulfonamide hydrochloride $\delta_H$ (400 MHz, CD$_3$OD) 1.25 (3H, t, J 7.3 Hz), 1.55-1.64 (1H, m), 1.80-1.87 (1H, m), 2.00-2.03 (1H, m), 2.17-2.20 (1H, m), 2.45 (3H, s), 2.58 (1H, dt, J 8.0, 15 Hz), 2.73 (3H, s), 2.85 (2H, m), 3.06-3.12 (2H, m), 3.55 (2H, m), 4.16 (2H, m), 4.30 (1H, m), 5.12 (1H, m), 5.86 (1H, m), 6.11-6.12 (1H, m), 7.47-7.50 (2H, m), 7.65-7.68 (2H, m); m/z (ES$^+$) 407 ([M+H]$^+$).

EXAMPLE 38

(1S,4R)-cis-3,N-Dimethyl-N-(4-(4-methoxypiperidin-1-yl)cyclopent-2-en-1-yl)benzenesulfonamide hydrochloride Step 1. (1S,4R)cis-3,N-Dimethyl-N-(4-(4-hydroxypiperidin-1-yl)cyclopent -2-en-1-yl)benzenesulfonamide Title compound prepared in an analogous manner to Example 33; $\delta_H$ (400 MHz, CDCl$_3$) 1.48-1.57 (4H, m), 1.86-1.88 (2H, m), 2.09-2.22 (3H, m), 2.43 (3H, s), 2.63-2.65 (1H, m), 2.67 (3H, s), 2.73-2.79 (1H, m), 3.55-3.56 (1H, m), 3.68 (1H, m), 4.97-4.99 (1H, m), 5.43-5.44 (1H, m), 5.93-5.95 (1H, m), 7.38-7.40 (2H, m), 7.60-7.63 (2H, m); m/z (ES$^+$) 351 ([M+H]$^+$).

Step 2. (1S4R)-cis-3,N-Dimethyl-N-(4-(4-methoxypiperidin-1-yl)cyclopent -2-en-1-yl)benzenesulfonamide hydrochloride A solution of (1S,4R)-cis-3,N-dimethyl-N-(4-(4-hydroxypiperidin-1-yl)cyclopent-2-en-1-yl)benzenesulfonamide (98 mg, 0.28 mmol) in N,N-dimethylformamide (3 ml) was cooled in an ice bath, treated with 60% sodium hydride in mineral oil (68 mg, 1.7 mmol) and stirred at 0° C. for 20 minutes. Iodomethane (0.02 ml, 0.3 mmol) was then added and the solution stirred at 0° C. for 30 minutes. Stirred to ambient temperature then diluted with ethyl acetate (10 ml). The organics were washed with water (2×10 ml) and dried (MgSO$_4$) before being concentrated in vacuo. The residue was purified by flash chromatography eluting with 5% methanol in dichloromethane to give (1S,4R)-cis-3,N-dimethyl-N-(4-(4-methoxypiperidin-1-yl)cyclopent-2-en-1-yl) benzenesulfonamide as a gum. This gum was dissolved in ethyl acetate (10 ml) and treated with 1N ethereal hydrogen chloride. The solid formed was recovered by filtration and recrystallised from methanol/diethyl ether to give the title compound (6 mg, 5%); $\delta_H$ (400 MHz, CD$_3$OD) 1.60-1.68 (1H, m), 1.75-1.82 (1H, m), 1.93 (1H, m), 2.11 (1H, m), 2.22-2.30 (1H, m), 2.44 (3H, s), 2.54-2.61 (1H, m), 2.72 (3H, s), 3.10-3.21 (3H, m), 3.34 (3H, s), 3.42-3.47 (1H, m), 3.60 (1H, m), 4.22 (1H, m), 5.09-5.13 (1H, m), 5.80-5.83 (1H, m), 6.12 (1H, m), 7.47-7.50 (2H, m), 7.65-7.68 (2H, m); In/z (ES$^+$) 365 ([M+H]$^+$).

The invention claimed is:
1. A compound of the formula I:

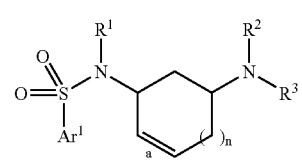

wherein:
n is 0;
bond a may be single or double, but is single when n is 1;
Ar$^1$ represents phenyl or thienyl, any of which optionally bears up to 3 substituents independently selected from halogen, OR$^5$, C$_{1-6}$alkyl and C$_{1-6}$alkyl-phenyl;
R$^1$ represents C$_{1-6}$alkyl;
R$^2$ and R$^3$ complete a piperidine, quinoline, tetrahydropyridine or tetrahydroisoquinoline ring, wherein the ring is optionally substituted with up to 3 substituents independently selected from halogen, CN, NO$_2$, CF$_3$, C$_{1-6}$alkyl, C$_{3-7}$cycloalkyl, phenyl, OR$^5$, N(R$^5$)$_2$, CO$_2$R$^5$, COR$^5$ and CON(R$^5$)$_2$;
R$^5$ represents H or C$_{1-4}$alkyl which is optionally substituted with halogen, phenyl, CF$_3$, OH, C$_{1-4}$alkoxy, C$_{1-4}$alkoxycarbonyl, amino, C$_{1-4}$alkylamino or di(C$_{1-4}$alkyl) amino;
or a pharmaceutically acceptable salt thereof.
2. The compound of claim 1 wherein Ar$^1$ is selected from the group consisting of: phenyl, 3-methylphenyl, 4-methylphenyl, 3-bromophenyl, 2-chlorophenyl, 3-chlorophenyl, 4-chlorophenyl, 3,4-dichlorophenyl, 2,4,5-trichlorophenyl, 4-chloro-2,5-dimethylphenyl, 3-hydroxyphenyl, 3-benzyloxyphenyl, 4,5-dichlorothiophen-2-yl and 4,5-dibromothiophene-2-yl.

3. The compound of claim 1 wherein $R^1$ represents methyl.

4. The compound of claim 1 wherein $R^2$ and $R^3$ complete a piperidine, quinoline, tetrahydropyridine or tetrahydroisoquinoline ring, wherein the ring is optionally substituted with up to 3 substituents independently selected from: $C_{1-6}$alkyl, $C_{3-7}$cycloalkyl, $OR^5$, $CO_2R^5$, $CF_3$ and phenyl.

5. The compound of claim 4 wherein $R^2$ and $R^3$ complete a piperidine, quinoline, tetrahydropyridine or tetrahydroisoquinoline ring, wherein the ring is optionally substituted with up to 3 substituents independently selected from: methyl, t-butyl, cyclohexyl, methoxy, ethoxycarbonyl, $CF_3$ and phenyl.

6. The compound of claim 1 wherein the —$NR^1SO_2Ar^1$ and the —$NR^2R^3$ functionalities are in the cis configuration.

7. The compound of claim 2 of the formula IA:

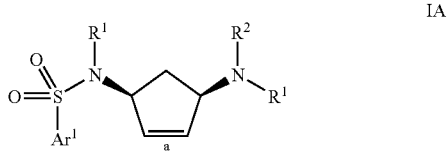

wherein bond a is a single bond or a double bond; or a pharmaceutically acceptable salt thereof.

8. A compound which is selected from the group consisting of:
cis-4,N-dimethyl-N-(3-(4-methylpiperidin-1-yl)cyclopentyl) -benzenesulfonamide;
cis-3,N-dimethyl-N-(3-(4-methylpiperidin-1-yl)cyclopentyl) -benzenesulfonamide;
cis-3-bromo-N-methyl-N-(3-(4-methylpiperidin-1-yl)cyclopentyl) -benzenesulfonamide;
cis-N-methyl-N-(3-(4-methylpiperidin-1-yl)cyclopentyl) -benzenesulfonamide;
cis-N-methyl-N-(3-(4-methylpiperidin-1-yl)cyclopentyl)-2,4,5-trichlorobenzenesulfonamide;
cis-3,4-dichloro-N-methyl-N-(3-(4-methylpiperidin-1-yl) cyclopentyl) -benzenesulfonamide;
cis-4,5-dibromo-N-methyl-N-(3-(4-methylpiperidin-1-yl) cyclopentyl) -thiophene-2-sulfonamide;
cis-3-benzyloxy-N-methyl-N-(3-(4-methylpiperidin-1-yl) cyclopentyl) -benzenesulfonamide;
cis-N-methyl-N-(3-(4-methylpiperidin-1-yl)cyclopentyl) naphthalene-1-sulfonamide;
cis-2-chloro-N-methyl-N-(3-(4-methylpiperidin-1-yl)cyclopentyl) -benzenesulfonamide;
cis-3-chloro-N-methyl-N-(3-(4-methylpiperidin-1-yl)cyclopentyl) -benzenesulfonamide;
cis-4-chloro-N-methyl-N-(3-(4-methylpiperidin-1-yl)cyclopentyl) -beuzenesulfonamide;
cis-3,5-dichloro-N-methyl-N-(3-(4-methylpiperidin-1-yl) -cyclopentyl)benzenesulfonamide;
cis-4,5-dichloro-N-methyl-N-(3-(4-methylpiperidin-1-yl) -cyclopentyl)thiophene-2-sulfonamide;
cis-4-chloro-2,5,N-trimethyl-N-(3-(4-methylpiperidin-1-yl) -cyclopentyl)benzenesulfonamide;
cis-3,N-dimethyl-N-(3-(4-phenyl-1,2,5,6-tetrahydropyridin-1-yl) -cyclopentyl)benzenesulfonamide;
cis-3 ,N-dimethyl-N-(3-(4-phenylpiperidin-1-yl)cyclopentyl) -benzenesulfonamide;
cis-3-hydroxy-N-methyl-N-(3-(4-methylpiperidin-1-yl) cyclopentyl) -benzenesulfonamide;
trans-3,N-dimethyl-N-(3-(1,2,3,4-tetrahydroisoquinolin-2-yl) -cyclopentyl)benzenesulfonamide;
cis-3,N-dimethyl-N-(3-(1,2,3,4-tetrahydroisoquinolin-2-yl) -cyclopentyl)benzenesulfonamide;
cis-3,N-dimethyl-N-(3-(4-trifluoromethylpiperidin-1-yl) cyclopentyl) -benzenesulfonamide;
cis-3,N-dimethyl-N-(3-(4-tert-butylpiperidin-1-yl)cyclopentyl) -benzenesulfonamide;
(1R,3S)-cis-3,N-dimethyl-N-(3-(4-trifluoromethylpiperidin-1-yl) -cyclopentyl)benzenesulfonamide;
(1R,3 S)-cis-4,5-dichloro-N-methyl-N-(3-(4-trifluoromethylpiperidin-1-yl) -cyclopentyl)thiophene-2-sulfonamide;
(1R,3S)-cis-4-chloro-2,5,N-trimethyl-N-(3-(4-trifluoromethylpiperidin-1-yl)cyclopentyl)benzenesulfonamide;
(1R,3S,4'aR,8'aS) or (1R,3S,4'aS,8'aR)-cis-3,N-dimethyl-N-(3-(decahydroisoquinolin-2-yl)cyclopentyl)benzenesulfonamide;
(1R,3S,4'aR,8'aS) or (1R,3S,4'aS,8'aR)-cis-4,5-dichloro-N-methyl-N -(3-(decahydroisoquinolin-2-yl)cyclopentyl)thiophene-2-sulfonamide;
cis-3,N-dimethyl-N-(4-(4-methylpiperidin-1-yl)cyclopent-2-en-1-yl) -benzenesulfonamide;
(1S,4R)-cis-3,N-dimethyl-N-(4-(4-methylpiperidin-1-yl) cyclopent-2-en-1-yl)benzenesulfonamide;
(1S,4R)-cis-3,N-dimethyl-N-(4-(4-trifluoromethylpiperidin-1-yl)-cyclopent -2-en-1-yl)benzenesulfonamide;
(1S,4R)-cis-3-chloro-N-methyl-N-(4-(4-methylpiperidin-1-yl)cyclopent-2-en-1-yl)benzenesulfonamide;
(1S,4R)-cis-4,5-dichloro-N-methyl-N-(4-(4-methylpiperidin-1-yl)cyclopent -2-en-1-yl)thiophene-2-sulfonamide;
(1S,4R)-cis-3,N-dimethyl-N-(4-(4-methyl-1,2,5,6-tetrahydropyridin-1-yl)cyclopent-2-en-1-yl)benzenesulfonamide;
(1S,4R)-cis-3,N-dimethyl-N-(4-(3 ,4-dimethyl-1,2,5,6-tetrahydropyridin-1-yl)cyclopent-2-en-1-yl)benzenesulfonamide;
(1S,4R,3'S)-cis-3,N-dimethyl-N-(4-(3-cyclohexylpiperidin-1-yl)cyclopent -2-en-1-yl)benzenesulfonamide;
(1S,4R,3'R)-cis-3,N-dimethyl-N-(4-(3-cyclohexylpiperidin-1-yl)cyclopent -2-en-1-yl)benzenesulfonamide;
(1S,4R,3'R)-cis-3,N-dimethyl-N-(4-(3-carboxyethylpiperidin-1-yl)cyclopent-2-en-1-yl)benzenesulfonamide; and
1S,4R)-cis-3,N-dimethyl-N-(4-(4-methoxypiperidin-1-yl)cyclopent-2-en-1-yl)benzenesulfonamide;
or a pharmaceutically acceptable salt thereof.

* * * * *